United States Patent
Fletcher et al.

(10) Patent No.: US 10,499,584 B2
(45) Date of Patent: Dec. 10, 2019

(54) **INDUSTRIAL HEMP *CANNABIS* CULTIVARS AND SEEDS WITH STABLE CANNABINOID PROFILES**

(71) Applicant: NEW WEST GENETICS, Ft. Collins, CO (US)

(72) Inventors: Richard S. Fletcher, Ft. Collins, CO (US); John McKay, Ft. Collins, CO (US)

(73) Assignee: New West Genetics, Ft. Collins, CO (US)

( * ) Notice: Subject to any disclaimer, the term of this patent is extended or adjusted under 35 U.S.C. 154(b) by 272 days.

(21) Appl. No.: 15/452,925

(22) Filed: Mar. 8, 2017

(65) Prior Publication Data

US 2017/0339907 A1    Nov. 30, 2017

Related U.S. Application Data

(60) Provisional application No. 62/342,658, filed on May 27, 2016.

(51) Int. Cl.
*A01H 5/12* (2018.01)
*C12C 7/28* (2006.01)

(52) U.S. Cl.
CPC .............. *A01H 5/12* (2013.01); *C12C 7/28* (2013.01)

(58) Field of Classification Search
CPC .............. A01H 5/00; A01H 5/12; A01H 6/28
See application file for complete search history.

(56) References Cited

U.S. PATENT DOCUMENTS

| | | |
|---|---|---|
| 5,252,490 A | 10/1993 | ElSohly et al. |
| 6,383,513 B1 | 5/2002 | Watts et al. |
| 6,403,126 B1 | 6/2002 | Webster et al. |
| 6,410,588 B1 | 6/2002 | Feldmann et al. |
| 6,503,532 B1 | 1/2003 | Murty et al. |
| 6,630,507 B1 | 10/2003 | Hampson et al. |
| 6,730,519 B2 | 5/2004 | Elsohly et al. |
| 6,949,582 B1 | 9/2005 | Wallace |
| 7,025,992 B2 | 4/2006 | Whittle et al. |
| 7,344,736 B2 | 3/2008 | Whittle et al. |
| 7,465,850 B2 | 12/2008 | Gipmans et al. |
| 7,579,517 B2 | 8/2009 | Renz et al. |
| 7,592,328 B2 | 9/2009 | Jarho et al. |
| 7,597,910 B2 | 10/2009 | McDowell, Jr. |
| 7,759,547 B2 | 7/2010 | Zou et al. |
| 7,807,711 B2 | 10/2010 | Korthout et al. |
| 7,807,870 B2 | 10/2010 | Geigenberger et al. |
| 8,034,843 B2 | 10/2011 | Whittle et al. |
| 8,071,641 B2 | 12/2011 | Weiss et al. |
| 8,119,697 B2 | 2/2012 | Mechoulam et al. |
| 8,222,292 B2 | 7/2012 | Goskonda et al. |
| 8,242,178 B2 | 8/2012 | Nagarkatti et al. |
| 8,293,786 B2 | 10/2012 | Stinchcomb et al. |
| 8,337,908 B2 | 12/2012 | Letzel et al. |
| 8,344,205 B2 | 1/2013 | Zank et al. |
| 8,445,034 B1 | 5/2013 | Coles, Jr. |
| 8,449,908 B2 | 5/2013 | Stinchcomb et al. |
| 8,470,874 B2 | 6/2013 | Musty et al. |
| 8,481,085 B2 | 7/2013 | Musty et al. |
| 8,586,767 B2 | 11/2013 | Travis |
| 8,628,796 B2 | 1/2014 | Kottayil et al. |
| 8,629,321 B2 | 1/2014 | Sallaud et al. |
| 8,632,825 B2 | 1/2014 | Velasco Diez et al. |
| 8,642,645 B2 | 2/2014 | Kelly |
| 8,673,368 B2 | 3/2014 | Guy et al. |
| 8,680,369 B2 | 3/2014 | Mosjidis |
| 8,697,095 B1 | 4/2014 | Medveczky et al. |
| 8,753,696 B1 | 6/2014 | Lewis |
| 8,758,826 B2 | 6/2014 | Bevier |
| 8,771,760 B2 | 7/2014 | Guy et al. |
| 8,778,418 B2 | 7/2014 | Bisterfeld Von Meer |
| 8,790,719 B2 | 7/2014 | Parolaro et al. |
| 8,808,734 B2 | 8/2014 | Winnicki |
| 8,846,409 B2 | 9/2014 | Flockhart et al. |
| 8,884,100 B2 | 11/2014 | Page et al. |
| 8,895,078 B2 | 11/2014 | Mueller |

(Continued)

FOREIGN PATENT DOCUMENTS

| | | |
|---|---|---|
| WO | 0103668 A1 | 1/2001 |
| WO | 02076480 A1 | 10/2002 |

(Continued)

OTHER PUBLICATIONS

*Cannabis sativa* L.—Botany and Biotechnology: 2017, Chandra, S.; Lata, H.; and ElSohly, M.A. (Eds.) Springer Nature; 474 pages.*
Bertoli, A. et al., Industrial Crops and Products, 2010, vol. 32; pp. 329-337.*
Moving Postcard; https://movingpostcard.com/weed-beer/ posted May 24, 2015 pp. 1-4.*
Montserrat-de la Paz, S. et al., Journal of Agricultural and Food Chemistry, Nov. 26, 2014, vol. 62; pp. 1105-1110. (Year: 2014).*

(Continued)

*Primary Examiner* — Russell Kallis

(74) *Attorney, Agent, or Firm* — McKee, Vorrhees & Sease, PLC

(57) ABSTRACT

According to the invention, there is provided novel hemp *Cannabis* cultivars with THC content of 0.2% by dry weight and a unique terpene profile. This invention thus relates to the seeds of hemp *Cannabis* cultivars of the invention, to the plants of hemp *Cannabis* cultivars of the invention, to plant parts of hemp *Cannabis* cultivars of the invention, to methods for producing a *Cannabis* cultivar by crossing the hemp *Cannabis* cultivars of the invention with another *Cannabis* cultivar, and to methods for producing a *Cannabis* cultivar containing in its genetic material one or more backcross conversion traits or transgenes and to the backcross conversion *Cannabis* plants and plant parts produced by those methods.

33 Claims, No Drawings

(56) References Cited

U.S. PATENT DOCUMENTS

| | | |
|---|---|---|
| 8,895,537 B2 | 11/2014 | Bannister et al. |
| 8,901,374 B2 | 12/2014 | Bauer et al. |
| 8,906,429 B1 | 12/2014 | Kolsky |
| 8,937,097 B2 | 1/2015 | Gutman et al. |
| 8,980,940 B2 | 3/2015 | Rossi et al. |
| 8,980,941 B2 | 3/2015 | Hospodor |
| 9,017,737 B2 | 4/2015 | Kikuchi et al. |
| 9,023,322 B2 | 5/2015 | Van Damme et al. |
| 9,029,423 B2 | 5/2015 | Whittle |
| 9,034,395 B2 | 5/2015 | Whittle et al. |
| 9,035,130 B2 | 5/2015 | De Meijer |
| 9,040,099 B1 | 5/2015 | Sugerman |
| 9,044,390 B1 | 6/2015 | Speier |
| 2003/0017216 A1 | 1/2003 | Schmidt et al. |
| 2003/0050334 A1 | 3/2003 | Murty et al. |
| 2003/0232101 A1 | 12/2003 | Travis |
| 2004/0138293 A1 | 7/2004 | Werner et al. |
| 2004/0229939 A1 | 11/2004 | Chowdhury et al. |
| 2005/0049298 A1 | 3/2005 | Goodwin et al. |
| 2005/0070596 A1 | 3/2005 | Baker et al. |
| 2005/0090468 A1 | 4/2005 | Jarvinen et al. |
| 2006/0135599 A1 | 6/2006 | Symonds et al. |
| 2006/0167283 A1 | 7/2006 | Flockhart et al. |
| 2006/0264647 A1 | 11/2006 | Field et al. |
| 2007/0060639 A1 | 3/2007 | Wermeling |
| 2008/0103193 A1 | 5/2008 | Castor et al. |
| 2008/0112895 A1 | 5/2008 | Kottayil et al. |
| 2008/0119544 A1 | 5/2008 | Guy et al. |
| 2008/0139667 A1 | 6/2008 | Robson et al. |
| 2008/0241339 A1 | 10/2008 | Mitchell et al. |
| 2008/0262079 A1 | 10/2008 | Mach et al. |
| 2009/0197941 A1 | 8/2009 | Guy et al. |
| 2009/0203094 A1 | 8/2009 | Cirpus et al. |
| 2009/0222951 A1 | 9/2009 | Cirpus et al. |
| 2009/0288226 A1 | 11/2009 | Hallahan et al. |
| 2009/0306221 A1 | 12/2009 | Guy et al. |
| 2010/0035978 A1 | 2/2010 | Guy et al. |
| 2010/0146670 A1 | 6/2010 | Tadege et al. |
| 2010/0158973 A1 | 6/2010 | Weiss et al. |
| 2010/0184130 A1 | 7/2010 | Koprowski et al. |
| 2010/0222437 A1 | 9/2010 | Munoz Blanco et al. |
| 2010/0249223 A1 | 9/2010 | Di Marzo et al. |
| 2010/0249248 A1 | 9/2010 | Ogura et al. |
| 2010/0286098 A1 | 11/2010 | Robson et al. |
| 2010/0292345 A1 | 11/2010 | Pertwee |
| 2010/0317729 A1 | 12/2010 | Guy et al. |
| 2011/0038949 A1 | 2/2011 | Oswal et al. |
| 2011/0046213 A1 | 2/2011 | Bhatarah et al. |
| 2011/0086113 A1 | 4/2011 | Velasco Diez et al. |
| 2011/0098348 A1 | 4/2011 | De Meijer |
| 2011/0256245 A1 | 10/2011 | Rosenblatt et al. |
| 2011/0276522 A1 | 11/2011 | Kehoe et al. |
| 2012/0004251 A1 | 1/2012 | Whalley et al. |
| 2012/0079627 A1 | 3/2012 | Gampala et al. |
| 2012/0095087 A1 | 4/2012 | Hyatt |
| 2012/0107300 A1 | 5/2012 | Schirripa |
| 2012/0165402 A1 | 6/2012 | Whalley et al. |
| 2012/0202891 A1 | 8/2012 | Stinchcomb et al. |
| 2012/0225136 A1 | 9/2012 | Whittle et al. |
| 2012/0231083 A1 | 9/2012 | Carley et al. |
| 2012/0245224 A1 | 9/2012 | Guy et al. |
| 2012/0252885 A1 | 10/2012 | Barbato |
| 2012/0311744 A1 | 12/2012 | Sirkowski |
| 2013/0067619 A1 | 3/2013 | Page et al. |
| 2013/0184354 A1 | 7/2013 | Jackson et al. |
| 2013/0245110 A1 | 9/2013 | Guy et al. |
| 2013/0274321 A1 | 10/2013 | Newland |
| 2013/0281523 A1 | 10/2013 | Letendre et al. |
| 2013/0295172 A1 | 11/2013 | Freeman |
| 2014/0030322 A1 | 1/2014 | Bosse et al. |
| 2014/0057251 A1 | 2/2014 | McKernan |
| 2014/0107192 A1 | 4/2014 | Maione et al. |
| 2014/0141476 A1 | 5/2014 | Page et al. |
| 2014/0221469 A1 | 8/2014 | Ross et al. |
| 2014/0228438 A1 | 8/2014 | Iuvone et al. |
| 2014/0243405 A1 | 8/2014 | Whalley et al. |
| 2014/0245494 A1 | 8/2014 | Cohen |
| 2014/0245495 A1 | 8/2014 | Cohen |
| 2014/0259228 A1 | 9/2014 | Cohen |
| 2014/0271940 A1 | 9/2014 | Wurzer |
| 2014/0298511 A1 | 10/2014 | Lewis et al. |
| 2014/0302185 A1 | 10/2014 | Cavalieri Manasse |
| 2014/0314757 A1 | 10/2014 | Sanchez et al. |
| 2014/0324660 A1 | 10/2014 | Bolno et al. |
| 2014/0330030 A1 | 11/2014 | Ferri |
| 2014/0335208 A1 | 11/2014 | Cawthorne et al. |
| 2014/0343136 A1 | 11/2014 | Izzo et al. |
| 2014/0357708 A1 | 12/2014 | Murty et al. |
| 2015/0004300 A1 | 1/2015 | Cavalieri Manasse |
| 2015/0037389 A1 | 2/2015 | Ragot et al. |
| 2015/0057341 A1 | 2/2015 | Perry |
| 2015/0057342 A1 | 2/2015 | Koren et al. |
| 2015/0086494 A1 | 3/2015 | Sekura et al. |
| 2015/0096230 A1 | 4/2015 | Ankner |
| 2015/0099019 A1 | 4/2015 | Johnson |
| 2015/0105455 A1 | 4/2015 | Bjorncrantz |
| 2015/0126754 A1 | 5/2015 | Fernandex Cid et al. |
| 2015/0152018 A1 | 6/2015 | Raber et al. |

FOREIGN PATENT DOCUMENTS

| | | |
|---|---|---|
| WO | 2006017892 A1 | 2/2006 |
| WO | 2009013506 A1 | 1/2009 |
| WO | 2009043395 A2 | 4/2009 |
| WO | 2010150245 A1 | 12/2010 |
| WO | 2011028144 A2 | 3/2011 |
| WO | 2012083414 A1 | 6/2012 |
| WO | 2013056269 A2 | 4/2013 |
| WO | 2013098402 A1 | 7/2013 |
| WO | 2014008192 A2 | 1/2014 |
| WO | 2014100231 A1 | 6/2014 |
| WO | 2014170649 A1 | 10/2014 |
| WO | 2014200350 A1 | 12/2014 |
| WO | 2014202989 A1 | 12/2014 |
| WO | 2015000064 A1 | 1/2015 |
| WO | 2015065180 A1 | 5/2015 |
| WO | 2015068052 A2 | 5/2015 |
| WO | 2015069763 A2 | 5/2015 |
| WO | 2015087058 A1 | 6/2015 |

OTHER PUBLICATIONS

Bertoli, A. et al., Industrial Crops and Products, 2010, vol. 32; pp. 329-337. (Year: 2010).*

Bertoli, A., Industrial Crops and Products, 2010; vol. 32, pp. 329-337. (Year: 2010).*

* cited by examiner

INDUSTRIAL HEMP CANNABIS CULTIVARS AND SEEDS WITH STABLE CANNABINOID PROFILES

CROSS-REFERENCE TO RELATED APPLICATIONS

This application claims priority to previously filed provisional application, U.S. Ser. No. 62/342,658, filed May 27, 2016, which is herein incorporated by reference in its entirety.

FIELD OF THE INVENTION

The present invention relates to the field of plant breeding. In particular, this invention relates specialty *cannabis* plants, cultivars and varieties, including methods for making and using said *cannabis* plants and compositions derived thereof.

BACKGROUND OF THE INVENTION

Industrial hemp is legally defined in the United States as *Cannabis* which contains 0.3% or less total sample dry weight of Δ9-Tetrahydrocannabinal (THC). THC content is normally well above the 0.30% threshold in modern varieties of *Cannabis*. THC is one of an estimated 85 cannabinoids (a class of terpenoids) synthesized in *Cannabis* species (El-Alfy et al., 2010, "Antidepressant-like effect of delta-9-tetrahydrocannabinol and other cannabinoids isolated from *Cannabis sativa* L", Pharmacology Biochemistry and Behavior 95 (4): 434-42).

Cannabinoids act on endogenous cannabinoid receptors located throughout the human body (Kreitzer and Stella, 2009, "The therapeutic potential of novel cannabinoid receptors", Pharmacology & Therapeutics 122 (2): 83-96). These receptors are present in humans because the human body manufactures a similar class of cannabinoids known as the endocannabinoids (Pertwee et al., 2010, "International Union of Basic and Clinical Pharmacology. LXXIX. Cannabinoid Receptors and Their Ligands: Beyond CB1 and CB2", Pharmacological Reviews 62 (4): 588-631).

The demand for the medicinal properties of cannabinoids derived from *Cannabis* is growing. Over the last 15 years, medicinal marijuana has gained similar regulatory ground as hemp. This is a reflection of consumer demand. In 2013, medical marijuana sales were estimated at 1.5 billion dollars. The medicinal effects of cannabinoids on human health continue to be validated as clinical research in this field expands and gains traction (Scott et al., 2014, "The Combination of Cannabidiol and Δ9-Tetrahydrocannabinol Enhances the Anticancer Effects of Radiation in an Orthotopic Murine Glioma Model", Molecular Cancer Therapeutics 13 (12): 2955-2967). The ability to create this medicine without THC is highly desired by many patients and regulatory agencies.

Terpenes are a large class of volatile organic hydrocarbons. In plants, they function as hormones (e.g. abscisic acid), as photosynthetic pigments (e.g. carotenoids) and are involved in many other vital physiological processes. Secondary terpenoids (secondary metabolites) account for the majority of terpenoid molecular structural diversity. The secondary terpenoids play a major role in the plant's response to environmental factors such as such as pathogen and photooxidative stresses (Tholl, 2006, "Terpene synthases and the regulation, diversity and biological roles of terpene metabolism", Current Opinion in Plant Biology 9 (3): 297-304). Apart from their functions in the plant, terpenes from hops (*Humulus lupulus*) such as myrcene and humulene serve as major aromatic and flavor compounds in beer. *Cannabis* synthesizes many terpenes including myrcene and humulene.

*Cannabis* normally reproduces under a dioecious system where male (staminate) and female (pistillate) flowers develop on separate plants. Monoecious plants (containing both male and female flowers) do exist. Female floral anatomy is characterized by pistils protruding from a calyx covered with resinous glandular trichomes. The glandular trichomes of the female flower are the primary site of cannabinoid synthesis. The female calyx contains ovaries and, therefore, is the site of seed development when fertilized by pollen produced by a male plant.

A vast majority of the *Cannabis* produced in the United States is done so by clonal propagation. Under this production scheme, meristems are cut from a selected plant and treated by various methods to induce rooting so that many, genetically identical progeny may be derived from the original. This is primarily done because breeding *Cannabis* seeds which consistently express a particular cannabinoid profile, often elevated for a particular cannabinoid (e.g. THC), is generally regarded as difficult. The simplicity of breeding varieties to be produced under a clonal reproduction system is quickly offset by the cost of clonal production, among other factors (Mckey et al., 2010, "The evolutionary ecology of clonally propagated domesticated plants", New Phytologist 186 (2): 318-332). There is a need in the industry for industrial hemp varieties which are reliably low in THC when produced in diverse environmental conditions and which express elevated levels of certain other cannabinoids. The present invention provides a *Cannabis* variety that consistently and reproducibly has nearly zero THC (thus qualifying as industrial hemp) and elevated levels of CBD.

There are numerous steps in the development of any novel, desirable plant germplasm. Plant breeding preferably begins with the analysis and definition of problems and weaknesses of the current germplasm, the establishment of program goals, and the definition of specific breeding objectives. The next step is preferable selection of germplasm that possess the traits to meet the program goals. The goal is to combine in a single variety or hybrid an improved combination of desirable traits from the parental germplasm.

SUMMARY OF THE INVENTION

According to the invention, there is provided novel Hemp *Cannabis* cultivars, having very low levels of Δ9-Tetrahydrocanabinal (THC). The cultivars exhibit on average less than about 0.2% THC. The cultivars also demonstrate elevated levels of advantageous cannabinoids such as cannabidol (CBD) and a ratio of CBD to THC of up to about 56:1. This invention thus relates to the seeds of the hemp *Cannabis* cultivars of the invention, to plants of the hemp *Cannabis* cultivars of the invention, to plant parts of the hemp *Cannabis* cultivars of the invention, to methods for producing a *Cannabis* cultivar produced by crossing the hemp *Cannabis* cultivars of the invention with another *Cannabis* cultivar, and to methods for producing a *Cannabis* cultivar containing in its genetic material one or more backcross conversion traits or transgenes and to the backcross conversion *Cannabis* plants and plant parts produced by those methods.

This invention also relates to *Cannabis* cultivars and plant parts derived from the hemp *Cannabis* cultivars of the invention, to methods for producing other *Cannabis* cultivars derived from hemp *Cannabis* cultivars of the invention and to the *Cannabis* cultivars and their parts derived by the use of those methods. This invention further relates to *Cannabis* cultivar seeds, plants and plant parts produced by crossing the hemp *Cannabis* cultivars of the invention or a backcross conversion of the cultivars of the invention with another *Cannabis* cultivar.

The invention further relates to products and compositions produced or purified from plants of the invention including the stalks, fibers, pulp, flowers, seeds, hemp and the like. Products produced form the hemp cultivars of the invention can include industrial textiles, building materials, foods, personal hygiene products such as soap, lotions, balms and the like, animal bedding, industrial products such as paints, inks, solvents and lubricants, consumer textiles, animal feed, etc. The invention also relates to use of the *Cannabis* plants, plant parts extracts and the like as a flavoring or aromatic component in malt beverages and the like.

DETAILED DESCRIPTION OF THE INVENTION

Definitions

In the description and tables which follow, a number of terms are used. In order to provide a clear and consistent understanding of the present invention, the following definitions are provided:

The invention provides *cannabis* plants. As used herein, the term "plant" refers to plants in the genus of *Cannabis* and plants derived thereof. Such as *cannabis* plants produced via asexual reproduction and via seed production.

The invention provides plant parts. As used herein, the term "plant part" refers to any part of a plant including but not limited to the embryo, shoot, root, stem, seed, stipule, leaf, petal, flower bud, flower, ovule, bract, trichome, branch, petiole, internode, bark, pubescence, tiller, rhizome, frond, blade, ovule, pollen, stamen, and the like. The two main parts of plants grown in some sort of media, such as soil or vermiculite, are often referred to as the "above-ground" part, also often referred to as the "shoots", and the "below-ground" part, also often referred to as the "roots". Plant part may also include certain extracts such as kief or hash which includes *cannabis* trichomes or glands.

The term "a" or "an" refers to one or more of that entity; for example, "a gene" refers to one or more genes or at least one gene. As such, the terms "a" (or "an"), "one or more" and "at least one" are used interchangeably herein. In addition, reference to "an element" by the indefinite article "a" or "an" does not exclude the possibility that more than one of the elements is present, unless the context clearly requires that there is one and only one of the elements.

As used herein, a "landrace" refers to a local variety of a domesticated plant species which has developed largely by natural processes, by adaptation to the natural and cultural environment in which it lives. The development of a landrace may also involve some selection by humans but it differs from a formal breed which has been selectively bred deliberately to conform to a particular formal, purebred standard of traits.

The invention provides plant cultivars. As used herein, the term "cultivar" means a group of similar plants that by structural features and performance (i.e., morphological and physiological characteristics) can be identified from other varieties within the same species. Furthermore, the term "cultivar" variously refers to a variety, strain or race of plant that has been produced by horticultural or agronomic techniques and is not normally found in wild populations. The terms cultivar, variety, strain and race are often used interchangeably by plant breeders, agronomists and farmers.

The term "variety" as used herein has identical meaning to the corresponding definition in the International Convention for the Protection of New Varieties of Plants (UPOV treaty), of Dec. 2, 1961, as Revised at Geneva on Nov. 10, 1972, on Oct. 23, 1978, and on Mar. 19, 1991. Thus, "variety" means a plant grouping within a single botanical taxon of the lowest known rank, which grouping, irrespective of whether the conditions for the grant of a breeder's right are fully met, can be i) defined by the expression of the characteristics resulting from a given genotype or combination of genotypes, ii) distinguished from any other plant grouping by the expression of at least one of the said characteristics and iii) considered as a unit with regard to its suitability for being propagated unchanged.

As used herein, the term "inbreeding" refers to the production of offspring via the mating between relatives. The plants resulting from the inbreeding process are referred to herein as "inbred plants" or "inbreds."

The term LOQ as used herein refers to the limit of quantitation for Gas Chromatography (GC) and High Performance Liquid Chromatography measurements.

The term secondary metabolites as used herein refers to organic compounds that are not directly involved in the normal growth, development, or reproduction of an organism. In other words, loss of secondary metabolites does not result in immediate death of said organism.

The term single allele converted plant as used herein refers to those plants which are developed by a plant breeding technique called backcrossing wherein essentially all of the desired morphological and physiological characteristics of an inbred are recovered in addition to the single allele transferred into the inbred via the backcrossing technique.

The invention provides samples. As used herein, the term "sample" includes a sample from a plant, a plant part, a plant cell, or from a transmission vector, or a soil, water or air sample.

The invention provides progeny. As used herein, the term "progeny" refers to any plant resulting from a vegetative or sexual reproduction from one or more parent plants or descendants thereof. For instance a progeny plant may be obtained by cloning or selfing of a parent plant or by crossing two parent plants and include selfings as well as the F1 or F2 or still further generations. An F1 is a first-generation progeny produced from parents at least one of which is used for the first time as donor of a trait, while offspring of second generation (F2) or subsequent generations (F3, F4, etc.) are specimens produced from selfings of F1's F2's etc. An F1 may thus be (and usually is) a hybrid resulting from a cross between two true breeding parents (true-breeding is homozygous for a trait), while an F2 may be (and usually is) an progeny resulting from self-pollination of said F1 hybrids.

The invention provides methods for crossing a first plant with a second plant. As used herein, the term "cross", "crossing", "cross pollination" or "cross-breeding" refer to the process by which the pollen of one flower on one plant is applied (artificially or naturally) to the ovule (stigma) of a flower on another plant. Backcrossing is a process in which a breeder repeatedly crosses hybrid progeny, for example a first generation hybrid (F1), back to one of the parents of the hybrid progeny. Backcrossing can be used to introduce one or more single locus conversions from one genetic background into another.

The term backcrossing is a process in which a breeder crosses progeny back to one of the parents one or more times, for example, a first generation hybrid $F_1$ with one of the parental genotype of the $F_1$ hybrid.

The invention provides donor plants and recipient plants. As used herein, "donor plants" refer to the parents of a variety which contains the gene or trait of interest which is desired to be introduced into a second variety (e.g., "recipient plants").

In some embodiments, the present invention provides methods for obtaining plant genotypes comprising recombinant genes. As used herein, the term "genotype" refers to the genetic makeup of an individual cell, cell culture, tissue, organism (e.g., a plant), or group of organisms.

In some embodiments, the present invention provides homozygotes. As used herein, the term "homozygote" refers to an individual cell or plant having the same alleles at one or more loci.

In some embodiments, the present invention provides homozygous plants. As used herein, the term "homozygous" refers to the presence of identical alleles at one or more loci in homologous chromosomal segments.

In some embodiments, the present invention provides hemizygotes. As used herein, the term "hemizygotes" or "hemizygous" refers to a cell, tissue, organism or plant in which a gene is present only once in a genotype, as a gene in a haploid cell or organism, a sex-linked gene in the heterogametic sex, or a gene in a segment of chromosome in a diploid cell or organism where its partner segment has been deleted.

In some embodiments, the present invention provides heterozygotes. As used herein, the terms "heterozygote" and "heterozygous" refer to a diploid or polyploid individual cell or plant having different alleles (forms of a given gene) present at least at one locus. In some embodiments, the cell or organism is heterozygous for the gene of interest which is under control of the synthetic regulatory element.

The invention provides methods for obtaining plant lines comprising recombinant genes. As used herein, the term "line" is used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (T0) plant regenerated from material of that line; (b) has a pedigree comprised of a T0 plant of that line; or (c) is genetically very similar due to common ancestry (e.g., via inbreeding or selfing). In this context, the term "pedigree" denotes the lineage of a plant, e.g. in terms of the sexual crosses affected such that a gene or a combination of genes, in heterozygous (hemizygous) or homozygous condition, imparts a desired trait to the plant.

The invention provides open-pollinated populations. As used herein, the terms "open-pollinated population" or "open-pollinated variety" refer to plants normally capable of at least some cross-fertilization, selected to a standard, that may show variation but that also have one or more genotypic or phenotypic characteristics by which the population or the variety can be differentiated from others. A hybrid, which has no barriers to cross-pollination, is an open-pollinated population or an open-pollinated variety.

The invention provides self-pollination populations. As used herein, the term "self-crossing", "self pollinated" or "self-pollination" means the pollen of one flower on one plant is applied (artificially or naturally) to the ovule (stigma) of the same or a different flower on the same plant.

The invention provides ovules and pollens of plants. As used herein when discussing plants, the term "ovule" refers to the female gametophyte, whereas the term "pollen" means the male gametophyte.

The invention provides plant tissue. As used herein, the term "plant tissue" refers to any part of a plant. Examples of plant organs include, but are not limited to the leaf, stem, root, tuber, seed, branch, pubescence, nodule, leaf axil, flower, pollen, stamen, pistil, petal, peduncle, stalk, stigma, style, bract, fruit, trunk, carpel, sepal, anther, ovule, pedicel, needle, cone, rhizome, stolon, shoot, pericarp, endosperm, placenta, berry, stamen, and leaf sheath.

The invention provides methods for obtaining plants comprising recombinant genes through transformation. As used herein, the term "transformation" refers to the transfer of nucleic acid (i.e., a nucleotide polymer) into a cell. As used herein, the term "genetic transformation" refers to the transfer and incorporation of DNA, especially recombinant DNA, into a cell.

The invention provides transformants comprising recombinant genes. As used herein, the term "transformant" refers to a cell, tissue or organism that has undergone transformation. The original transformant is designated as "T0" or "$T_0$." Selfing the T0 produces a first transformed generation designated as "T1" or "$T_1$."

In some embodiments, the present invention provides organisms with recombinant genes. As used herein, an "organism" refers any life form that has genetic material comprising nucleic acids including, but not limited to, prokaryotes, eukaryotes, and viruses. Organisms of the present invention include, for example, plants, animals, fungi, bacteria, and viruses, and cells and parts thereof.

As used herein, the term "female" refers to *Cannabis* plants carrying only pistillate flowers and devoid of pollen. The term "bud" refers to *Cannabis* female floral tissue collected prior to seed harvest from the apical meristems. The term "chaff" refers to *Cannabis* bud tissue collected after threshing and separation of physiologically mature seed from the bud. The term "male" refers to *Cannabis* plants carrying only staminate flowers producing pollen.

*Cannabis*

*Cannabis* has long been used for drug and industrial purposes including fiber, seed and seed oils, and for medicinal purposes. Industrial hemp fiber products are made from *Cannabis* plants selected to produce an abundance of stalk tissue from which fiber is created.

*Cannabis* plants produce a unique family of terpenophenolic compounds called cannabinoids. Cannabinoids, terpenoids, and other compounds are secreted by glandular trichomes that occur most abundantly on the floral calyxes and bracts of female plants. As a drug it usually comes in the form of dried flower buds (marijuana), resin (hashish), or various extracts collectively known as hashish oil. There are at least 483 identifiable chemical constituents known to exist in the *cannabis* plant (Rudolf Brenneisen, 2007, Chemistry and Analysis of Phytocannabinoids (cannabinoids produced by *cannabis*) and other *Cannabis* Constituents, In Marijuana and the Cannabinoids, ElSohly, ed.; incorporated herein by reference) and at least 85 different cannabinoids have been isolated from the plant (El-Alfy, Abir T, et al., 2010, "Antidepressant-like effect of delta-9-tetrahydrocannabinol and other cannabinoids isolated from *Cannabis sativa* L", Pharmacology Biochemistry and Behavior 95 (4): 434-42; incorporated herein by reference). The two cannabinoids usually produced in greatest abundance are cannabidiol (CBD) and/or Δ-9-tetrahydrocannabinol (THC). THC is psychoactive while CBD is not. See, ElSohly, ed. (Marijuana and the Cannabinoids, Humana Press Inc., 321 papers, 2007), which is incorporated herein by reference in its entirety, for a detailed description and literature review on the cannabinoids found in marijuana.

Cannabinoids are the most studied group of secondary metabolites in Cannabis. Most exist in two forms, as acids and in neutral (decarboxylated) forms. The acid form is designated by an "A" at the end of its acronym (i.e. THCA). The phytocannabinoids are synthesized in the plant as acid forms, and while some decarboxylation does occur in the plant, it increases significantly post-harvest and the kinetics increase at high temperatures. (Sanchez and Verpoorte 2008). The biologically active forms for human consumption are the neutral forms. Decarboxylation is usually achieved by thorough drying of the plant material followed by heating it, often by either combustion, vaporization, or heating or baking in an oven. Unless otherwise noted, references to cannabinoids in a plant include both the acidic and decarboxylated versions (e.g., CBD and CBDA).

The cannabinoids in cannabis plants include, but are not limited to, Δ 9 Tetrahydrocannabinol (.Δ9-THC), Δ. 8-Tetrahydrocannabinol (Δ8-THC), Cannabichromene (CBC), Cannabicyclol (CBL), Cannabidiol (CBD), Cannabielsoin (CBE), Cannabigerol (CBG), Cannabinidiol (CBND), Cannabinol (CBN), Cannabitriol (CBT), and their propyl homologs, including, but are not limited to cannabidivarin (CBDV), Δ.9-Tetrahydrocannabivarin (THCV), cannabichromevarin (CBCV), and cannabigerovarin (CBGV). See Holley et al. (Constituents of Cannabis sativa L. XI Cannabidiol and cannabichromene in samples of known geographical origin, J. Pharm. Sci. 64:892-894, 1975) and De Zeeuw et al. (Cannabinoids with a propyl side chain in Cannabis, Occurrence and chromatographic behavior, Science 175:778-779), each of which is herein incorporated by reference in its entirety for all purposes. Non-THC cannabinoids can be collectively referred to as "CBs", wherein CBs can be one of THCV, CBDV, CBGV, CBCV, CBD, CBC, CBE, CBG, CBN, CBND, and CBT cannabinoids.

Cannabis Chemistry

Cannabinoids are a class of diverse chemical compounds that activate cannabinoid receptors of the human endocannabinoid physiological system. Cannabinoids produced by plants are called phytocannabinoids, a.k.a., natural cannabinoids, herbal cannabinoids, and classical cannabinoids. At least 85 different cannabinoids have been isolated from the cannabis plants (El-Alfy et al., 2010, "Antidepressant-like effect of delta-9-tetrahydrocannabinol and other cannabinoids isolated from Cannabis sativa L", Pharmacology Biochemistry and Behavior 95 (4): 434-42; Brenneisen, supra). Typical cannabinoids isolated from cannabis plants include, but are not limited to, Tetrahydrocannabinol (THC), Cannabidiol (CBD), CBG (Cannabigerol), CBC (Cannabichromene), CBL (Cannabicyclol), CBV (Cannabivarin), THCV (Tetrahydrocannabivarin), CBDV (Cannabidivarin), CBCV (Cannabichromevarin), CBGV (Cannabigerovarin), and CBGM (Cannabigerol Monomethyl Ether). In the Cannabis plant, cannabinoids are synthesized and accumulated as cannabinoid acids (e.g., cannabidiolic acid (CBDA)). When the herbal product is dried, stored, or heated, the acids decarboxylize gradually or completely into neutral forms (e.g., CBDA→CBD).

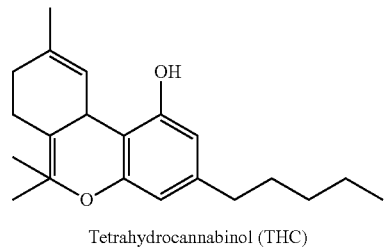

Tetrahydrocannabinol (THC)

Known as delta-9-tetrahydrocannabinol (Δ9-THC), THC is the principal psychoactive constituent (or cannabinoid) of the cannabis plant. The initially synthesized and accumulated form in plant is THC acid (THCA).

THC has mild to moderate analgesic effects, and Cannabis can be used to treat pain by altering transmitter release on dorsal root ganglion of the spinal cord and in the periaqueductal gray. Other effects include relaxation, alteration of visual, auditory, and olfactory senses, fatigue, and appetite stimulation. THC has marked antiemetic properties, and may also reduce aggression in certain subjects (Hoaken (2003). "Drugs of abuse and the elicitation of human aggressive behavior". Addictive Behaviors 28: 1533-1554).

The pharmacological actions of THC result from its partial agonist activity at the cannabinoid receptor CB1, located mainly in the central nervous system, and the CB2 receptor, mainly expressed in cells of the immune system (Pertwee, 2006, "The pharmacology of cannabinoid receptors and their ligands: An overview". International Journal of Obesity 30: S13-S18) The psychoactive effects of THC are primarily mediated by its activation of CB1G-protein coupled receptors, which result in a decrease in the concentration of the second messenger molecule cAMP through inhibition of adenylate cyclase (Elphick et al., 2001, "The neurobiology and evolution of cannabinoid signaling". Philosophical Transactions of the Royal Society B: Biological Sciences 356 (1407): 381-408.) It is also suggested that THC has an anticholinesterase action which may implicate it as a potential treatment for Alzheimer's and Myasthenia (Eubanks et al., 2006, "A Molecular Link Between the Active Component of Marijuana and Alzheimer's Disease Pathology". Molecular Pharmaceutics 3 (6): 773-7.)

In the cannabis plant, THC occurs mainly as tetrahydrocannabinolic acid (THCA, 2-COOH-THC). Geranyl pyrophosphate and olivetolic acid react, catalyzed by an enzyme to produce cannabigerolic acid, which is cyclized by the enzyme THC acid synthase to give THCA. Over time, or when heated, THCA is decarboxylated to produce THC. The pathway for THCA biosynthesis is similar to that which produces the bitter acid humulone in hops. See Fellermeier et al., (1998, "Prenylation of olivetolate by a hemp transferase yields cannabigerolic acid, the precursor of tetrahydrocannabinol". FEBS Letters 427 (2): 283-5); de Meijer et al. I, II, III, and IV (I: 2003, Genetics, 163:335-346; II: 2005, Euphytica, 145:189-198; III: 2009, Euphytica, 165:293-311; and IV: 2009, Euphytica, 168:95-112.)

CBD is a cannabinoid found in cannabis. Cannabidiol has displayed sedative effects in animal tests (Pickens, 1981, "Sedative activity of cannabis in relation to its delta'-trans-tetrahydrocannabinol and cannabidiol content". Br. J. Pharmacol. 72 (4): 649-56). Some research, however, indicates that CBD can increase alertness, and attenuate the memory-impairing effect of THC. (Nicholson et al., June 2004, "Effect of Delta-9-tetrahydrocannabinol and cannabidiol on nocturnal sleep and early-morning behavior in young adults"

J Clin Psychopharmacol 24 (3): 305-13; Morgan et al., 2010, "Impact of cannabidiol on the acute memory and psychotomimetic effects of smoked *cannabis*: naturalistic study, The British Journal of Psychiatry, 197:258-290). It may decrease the rate of THC clearance from the body, perhaps by interfering with the metabolism of THC in the liver. Medically, it has been shown to relieve convulsion, inflammation, anxiety, and nausea, as well as inhibit cancer cell growth (Mechoulam, et al., 2007, "Cannabidiol—recent advances". Chemistry & Biodiversity 4 (8): 1678-1692.) Recent studies have shown cannabidiol to be as effective as atypical antipsychotics in treating schizophrenia (Zuardi et al., 2006, "Cannabidiol, a *Cannabis sativa* constituent, as an antipsychotic drug" Braz. J. Med. Biol. Res. 39 (4): 421-429.). Studies have also shown that it may relieve symptoms of dystonia (Consroe, 1986, "Open label evaluation of cannabidiol in dystonic movement disorders". The International journal of neuroscience 30 (4): 277-282). CBD reduces growth of aggressive human breast cancer cells in vitro and reduces their invasiveness (McAllister et al., 2007, "Cannabidiol as a novel inhibitor of Id-1 gene expression in aggressive breast cancer cells". Mol. Cancer. Ther. 6 (11): 2921-7.)

Cannabidiol has shown to decrease activity of the limbic system (de Souza Crippa et al., "Effects of Cannabidiol (CBD) on Regional Cerebral Blood Flow". Neuropsychopharmacology 29 (2): 417-426) and to increase social interaction which is often decreased by THC (Malon et al., "Cannabidiol reverses the reduction in social interaction produced by low dose Δ9-tetrahydrocannabinol in rats". Pharmacology Biochemistry and Behavior 93 (2): 91-96.) It's also shown that Cannabidiol reduces anxiety in social anxiety disorder (Bergamaschi et al., 2003, "Cannabidiol Reduces the Anxiety Induced by Simulated Public Speaking in Treatment-Naive Social Phobia Patients". Neuropsychopharmacology 36 (6): 1219-1226). Cannabidiol has also been shown as being effective in treating an often drug-induced set of neurological movement disorders known as dystonia (Snider et al., 1985, "Beneficial and Adverse Effects of Cannabidiol in a Parkinson Patient with Sinemet-Induced Dystonic Dyskinesia". Neurology, (Suppl 1): 201.) Morgan et al. reported that strains of *cannabis* which contained higher concentrations of Cannabidiol did not produce short-term memory impairment vs. strains which contained similar concentrations of THC (2010, "Impact of cannabidiol on the acute memory and psychotomimetic effects of smoked *cannabis*: naturalistic study: naturalistic study [corrected]". British Journal of Psychiatry 197 (4): 285-90.)

Cannabidiol acts as an indirect antagonist of cannabinoid agonists. CBD is an antagonist at the putative new cannabinoid receptor, GPR55. Cannabidiol has also been shown to act as a 5-HT1A receptor agonist, an action which is involved in its antidepressant, anxiolytic, and neuroprotective effects. Cannabidiol is also an allosteric modulator at the Mu and Delta opioid receptor sites.

*Cannabis* produces CBD-carboxylic acid through the same metabolic pathway as THC, until the last step, where CBDA synthase performs catalysis instead of THCA synthase. See Marks et al. (2009, "Identification of candidate genes affecting Δ9-tetrahydrocannabinol biosynthesis in *Cannabis sativa*". Journal of Experimental Botany 60 (13): 3715-3726) and Meijer et al. I, II, III, and IV. Non-limiting examples of CBD variants include:

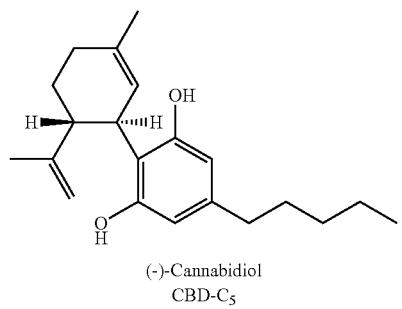

(-)-Cannabidiol
CBD-C$_5$

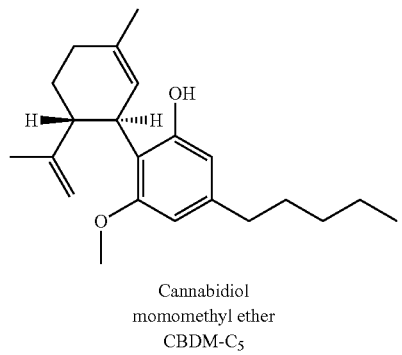

Cannabidiol monomethyl ether
CBDM-C$_5$

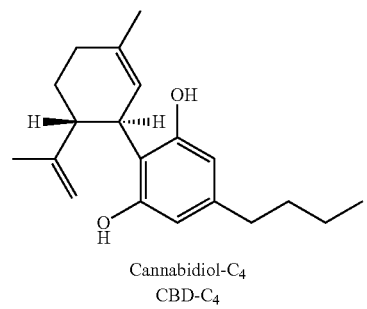

Cannabidiol-C$_4$
CBD-C$_4$

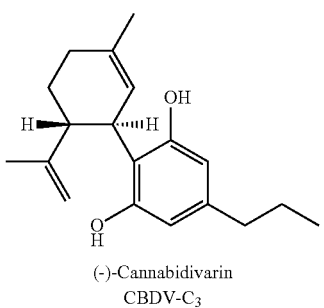

(-)-Cannabidivarin
CBDV-C$_3$

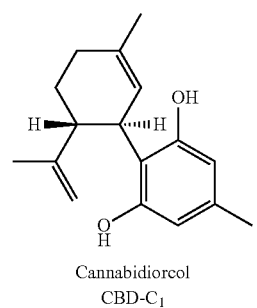

Cannabidiorcol
CBD-C$_1$

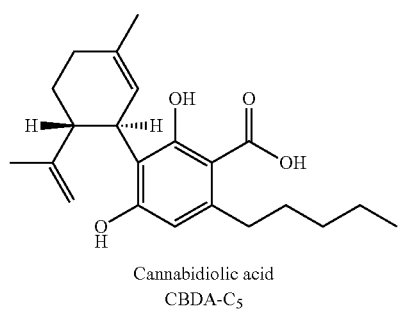

Cannabidiolic acid
CBDA-C$_5$

-continued

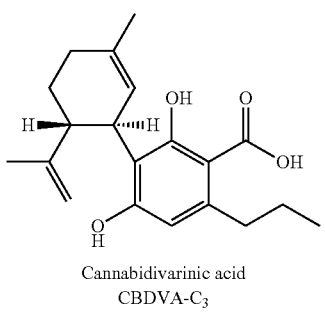

Cannabidivarinic acid
CBDVA-C$_3$

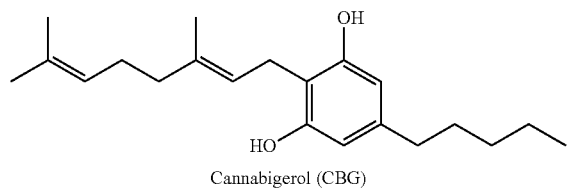

Cannabigerol (CBG)

CBG is a non-psychoactive cannabinoid found in the *Cannabis* genus of plants. Cannabigerol is found in higher concentrations in hemp rather than in varieties of *Cannabis* cultivated for high THC content and their corresponding psychoactive properties. Cannabigerol has been found to act as a high affinity α-2-adrenergic receptor agonist, moderate affinity 5-HT1A receptor antagonist, and low affinity CB.sub.1 receptor antagonist. It also binds to the CB2 receptor. Cannabigerol has been shown to relieve intraocular pressure, which may be of benefit in the treatment of glaucoma (Craig et al. 1984, "Intraocular pressure, ocular toxicity and neurotoxicity after administration of cannabinol or cannabigerol" Experimental eye research 39 (3):251-259). Cannabigerol has also been shown to reduce depression in animal models (U.S. patent application Ser. No. 11/760,364). Non-limiting examples of CBG variants include:

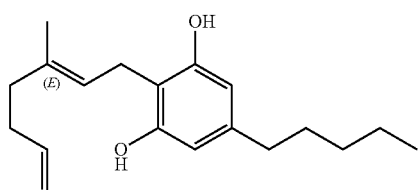

Cannabigerol
(E)-CBG-C$_5$

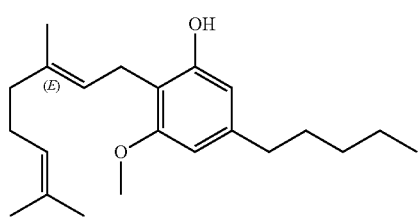

Cannabigerol
monomethyl ether
(E)-CBGM-C$_5$ A

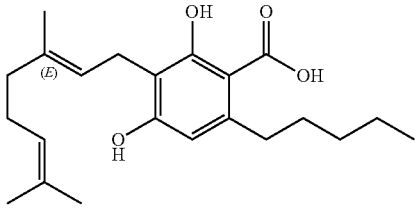

Cannabinerolic acid A
(Z)-CBGA-C$_5$ A

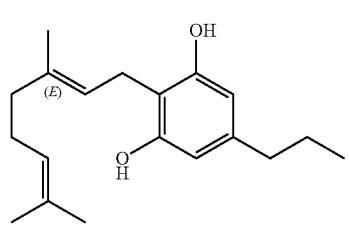

Cannabigerovarin
(E)-CBGV-C$_3$

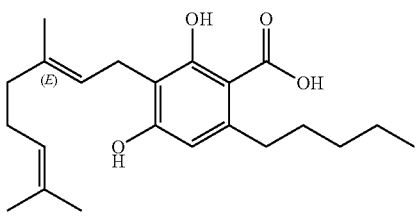

Cannabigerolic acdid A
(E)-CBGA-C$_5$ A

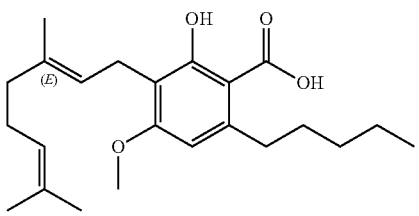

Cannabigerolic acdid A
monomethyl ether
(E)-CBGAM-C$_5$ A

CBN is a psychoactive substance cannabinoid found in *Cannabis sativa* and *Cannabis indica/afghanica*. It is also a metabolite of tetrahydrocannabinol (THC). CBN acts as a weak agonist of the CB1 and CB2 receptors, with lower affinity in comparison to THC.

CBC bears structural similarity to the other natural cannabinoids, including tetrahydrocannabinol, tetrahydrocannabivarin, cannabidiol, and cannabinol, among others. Evidence has suggested that it may play a role in the anti-inflammatory and anti-viral effects of *cannabis*, and may contribute to the overall analgesic effects of *cannabis*. Non-limiting examples of CBC variants include:

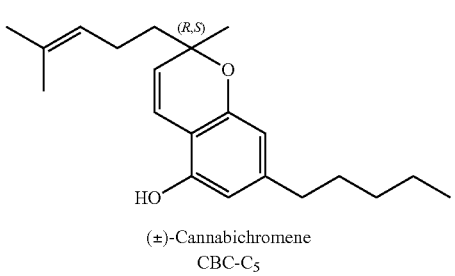

(±)-Cannabichromene
CBC-C5

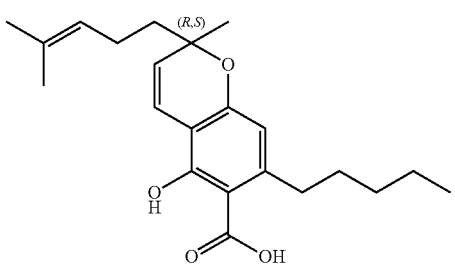

(±)-Cannabichromenic acid A
CBCA-C5 A

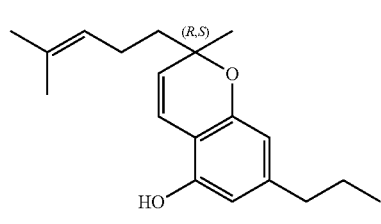

(±)-Cannabivarichromene,
(±)-Cannabichromevarin
CBCV-C3

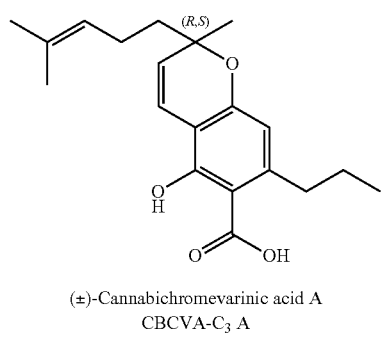

(±)-Cannabichromevarinic acid A
CBCVA-C3 A

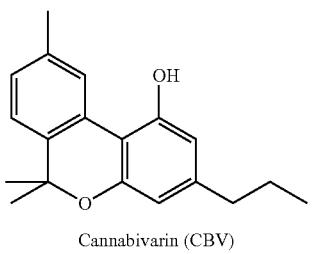

Cannabivarin (CBV)

Cannabivarin, also known as cannabivarol or CBV, is a non-psychoactive cannabinoid found in minor amounts in the hemp plant *Cannabis sativa*. It is an analog of cannabinol (CBN) with the side chain shortened by two methylene bridges (—CH2-). CBV is an oxidation product of tetrahydrocannabivarin (THCV, THV).

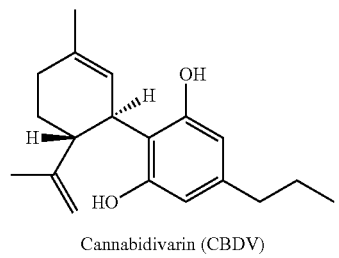 [SMILES: C=C(C)[C@@H]1CCC(C)=C[C@H]1c1c(O)cc(CCC)cc1O]

Cannabidivarin (CBDV)

CBDV is a non-psychoactive cannabinoid found in *Cannabis*. It is a homolog of cannabidiol (CBD), with the side-chain shortened by two methylene bridges (CH2 units). Cannabidivarin has been found reduce the number and severity of seizures in animal models (U.S. patent application Ser. No. 13/075,873). Plants with relatively high levels of CBDV have been reported in feral populations of *C. indica* (=*C. sativa* ssp. *indica* var. *kafiristanica*) from northwest India, and in hashish from Nepal.

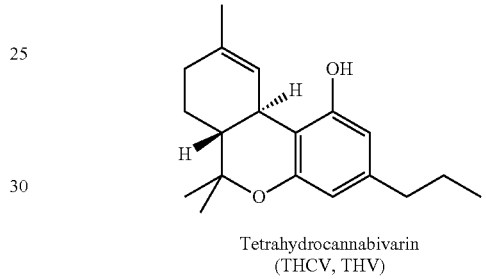

Tetrahydrocannabivarin
(THCV, THV)

THCV, or THV is a homologue of tetrahydrocannabinol (THC) having a propyl (3-carbon) side chain. This terpenophenolic compound is found naturally in *Cannabis*, sometimes in significant amounts. Plants with elevated levels of propyl cannabinoids (including THCV) have been found in populations of *Cannabis sativa* L. ssp. *indica* (=*Cannabis indica* Lam.) from China, India, Nepal, Thailand, Afghanistan, and Pakistan, as well as southern and western Africa. THCV has been shown to be a CB1 receptor antagonist, i.e. it blocks the effects of THC. Tetrahydrocannabinol has been shown to increase metabolism, help weight loss and lower cholesterol in animal models (U.S. patent application Ser. No. 11/667,860).

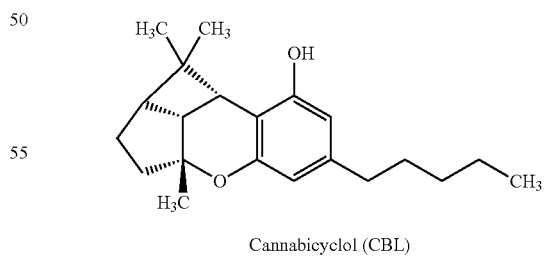

Cannabicyclol (CBL)

Cannabicyclol (CBL) is a non-psychotomimetic cannabinoid found in the *Cannabis* species. CBL is a degradative product like cannabinol. Light converts cannabichromene to CBL. Non-limiting examples of CBL variants include:

Terpenes and Terpenoids in *Cannabis* Plants

Terpenes are a large and diverse class of organic compounds, produced by *Cannabis* plants. They are often strong smelling and thus may have had a protective function. Terpenes are derived biosynthetically from units of isoprene, which has the molecular formula $C_5.H_8$. The basic molecular formulae of terpenes are multiples of that, $(C_5H_8)_n$ where n is the number of linked isoprene units. The isoprene units may be linked together "head to tail" to form linear chains or they may be arranged to form rings. Non-limiting examples of terpenes include Hemiterpenes, Monoterpenes, Sesquiterpenes, Diterpenes, Sesterterpenes, Triterpenes, Sesquarterpenes, Tetraterpenes, Polyterpenes, and Norisoprenoids.

Terpenoids, a.k.a. isoprenoids, are a large and diverse class of naturally occurring organic chemicals similar to terpenes, derived from five-carbon isoprene units assembled and modified in thousands of ways. Most are multicyclic structures that differ from one another not only in functional groups but also in their basic carbon skeletons. Plant terpenoids are used extensively for their aromatic qualities. They play a role in traditional herbal remedies and are under investigation for antibacterial, antineoplastic, and other pharmaceutical functions. The terpene Linalool for example, has been found to have anticonvulsant properties (Elisabetsky et al., Phytomedicine, May 6(2):107-13 1999). Well-known terpenoids include citral, menthol, camphor, salvinorin A in the plant *Salvia divinorum*, and the cannabinoids found in *Cannabis*. Non-limiting examples of terpenoids include, Hemiterpenoids, 1 isoprene unit (5 carbons); Monoterpenoids, 2 isoprene units (10C); Sesquiterpenoids, 3 isoprene units (15C); Diterpenoids, 4 isoprene units (20C) (e.g. ginkgolides); Sesterterpenoids, 5 isoprene units (25C); Triterpenoids, 6 isoprene units (30C) (e.g. sterols); Tetraterpenoids, 8 isoprene units (40C) (e.g. carotenoids); and Polyterpenoid with a larger number of isoprene units.

In addition to cannabinoids, *Cannabis* also produces over 120 different terpenes (Russo 2011, Taming THC: potential *cannabis* synergy and phytocannabinoid-terpenoid entourage effects, British Journal of Pharmacology, 163:1344-1364). Within the context and verbiage of this document the terms 'terpenoid' and 'terpene' are used interchangeably. Cannabinoids are odorless, so terpenoids are responsible for the unique odor of *Cannabis*, and each variety has a slightly different profile that can potentially be used as a tool for identification of different varieties or geographical origins of samples (Hillig 2004. "A chemotaxonomic analysis of terpenoid variation in *Cannabis*" Biochem System and Ecology 875-891). It also provides a unique and complex organoleptic profile for each variety that is appreciated by both novice users and connoisseurs. In addition to many circulatory and muscular effects, some terpenes interact with neurological receptors. A few terpenes produced by *Cannabis* plants also bind weakly to Cannabinoid receptors. Some terpenes can alter the permeability of cell membranes and allow in either more or less THC, while other terpenes can affect serotonin and dopamine chemistry as neurotransmitters. Terpenoids are lipophilic, and can interact with lipid membranes, ion channels, a variety of different receptors (including both G-protein coupled odorant and neurotransmitter receptors), and enzymes. Some are capable of absorption through human skin and passing the blood brain barrier.

Generally speaking, terpenes are considered to be pharmacologically relevant when present in concentrations of at least 0.05% in plant material (Hazekamp and Fischedick 2010. "Metabolic fingerprinting of *Cannabis sativa* L., cannabinoids and terpenoids for chemotaxonomic and drug standardization purposes" Phytochemistry 2058-73; Russo 2011, Taming THC: potential *cannabis* synergy and phytocannabinoid-terpenoid entourage effects, British Journal of Pharmacology, 163:1344-1364). Thus, although there are an estimated 120 different terpenes, only a few are produced at high enough levels to be detectable, and fewer still which are able to reach pharmacologically relevant levels.

A *Cannabis* terpene profile is includes the absolute and relative values of the 25 of the most measured terpenes disclosed herein, including but not limited to: terpinolene, alpha phellandrene, beta ocimene, carene, limonene, gamma terpinene, alpha pinene, alpha terpinene, beta pinene, camphene, alpha terpineol, alpha humulene, beta caryophyllene, linalool, caryophyllene oxide, and myrcene. Both experts and consumers believe that there are biochemical and phenomenological differences between different varieties of *cannabis*, which are attributed to their unique relative cannabinoid and terpenoid ratios. This is known as the entourage effect and is generally considered to result in plants providing advantages over only using the natural products that are isolated from them (Russo 2011, Taming THC: potential *cannabis* synergy and phytocannabinoid-terpenoid entourage effects, British Journal of Pharmacology, 163: 1344-1364).

Terpenoids can be extracted from the plant material by steam distillation (giving you essential oil) or vaporization, however the yield varies greatly by plant tissue, type of extraction, age of material, and other variables (McPartland and Russo 2001 "*Cannabis* and *Cannabis* Extracts: Greater Than the Sum of Their Parts?" Hayworth Press). Typically, the yield of terpenoids in *Cannabis* is less than 1% by weight on analysis; however, it is thought that they may comprise up to 10% of the trichome content. Monoterpenoids are especially volatile, thus decreasing their yield relative to sesquiterpenoids (Russo 2011, Taming THC: potential *cannabis* synergy and phytocannabinoid-terpenoid entourage effects, British Journal of Pharmacology, 163:1344-1364).

D-Limonene is a monoterpenoid that is widely distributed in nature and often associated with citrus. It has strong anxiolytic properties in both mice and humans, apparently increasing serotonin and dopamine in mouse brain. D-limonene has potent antidepressant activity when inhaled. It is also under investigation for a variety of different cancer treatments, with some focus on its hepatic metabolite, perillic acid. There is evidence for activity in the treatment of dermatophytes and gastro-oesophageal reflux, as well as having general radical scavenging properties (Russo 2011, Taming THC: potential *cannabis* synergy and phytocannabinoid-terpenoid entourage of British Journal of Pharmacology, 163:1344-1364).

β-Myrcene is a monoterpenoid also found in *cannabis*, and has a variety of pharmacological effects. It is often associated with a sweet fruit like taste. It reduces inflammation, aids sleep, and blocks hepatic carcinogenesis, as well as acting as an analgesic and muscle relaxant in mice. When βmyrcene is combined with Δ9-THC it could intensify the sedative effects of Δ9-THC, causing the well-known "couch-lock" effect that some *Cannabis* users experience (Russo 2011, Taming THC: potential *cannabis* synergy and phytocannabinoid-terpenoid entourage effects, British Journal of Pharmacology, 163:1344-1364).

D-Linalool is a monoterpenoid with very well-known anxiolytic effects. It is often associated with lavender, and frequented used in aromatherapy for its sedative impact. It acts as a local anaesthetic and helps to prevent scarring from burns, is anti-nociceptive in mice, and shows antiglutamatergic and anticonvulsant activity. Its effects on glutamate and GABA neurotransmitter systems are credited with giving it its sedative, anxiolytic, and anticonvulsant activities (Russo 2011, Taming THC: potential *cannabis* synergy and phytocannabinoid-terpenoid entourage effects, British Journal of Pharmacology, 163:1344-1364).

α-Pinene is a monoterpene common in nature, also with a plethora of effects on mammals and humans. It acts as an acetylcholinesterase inhibitor which aids memory and counteracts the short-term memory loss associated with Δ9-THC intoxication, is an effective antibiotic agent, and shows some activity against MRSA. In addition, α-pinene is a bronchodilator in humans and has anti-inflammatory properties via the prostaglandin E-1 pathway (Russo 2011, Taming THC: potential *cannabis* synergy and phytocannabinoid-terpenoid entourage effects, British Journal of Pharmacology, 163: 1344-1364).

β-Caryophyllene is often the most predominant sesquiterpenoid in *cannabis*. It is less volatile than the monoterpenoids, thus it is found in higher concentrations in material that has been processed by heat to aid in decarboxylation. It is very interesting in that it is a selective full agonist at the CB2 receptor, which makes it the only phytocannabinoid found outside the *cannabis* genus. In addition, it has anti-inflammatory and gastric cytoprotective properties, and may even have anti-malarial activity.

Caryophyllene oxide is another sesquiterpenoid found in *cannabis*, which has antifungal and anti-platelet aggregation properties. As an aside, it is also the molecule that drug-sniffing dogs are trained to find (Russo 2011, Taming THC: potential *cannabis* synergy and phytocannabinoid-terpenoid entourage effects, British Journal of Pharmacology, 163: 1344-1364).

Nerolidol is a sesquiterpene that is often found in citrus peels that exhibits a range of interesting properties. It acts as a sedative, inhibits fungal growth, and has potent anti-malarial and antileishmanial activity. It also alleviated colon adenomas in rats (Russo 2011, Taming THC: potential *cannabis* synergy and phytocannabinoid-terpenoid entourage effects, British Journal of Pharmacology, 163:1344-1364). Phytol is a diterpene often found in *cannabis* extracts. It is a degradation product of chlorophyll and tocopherol. It increases GABA expression and therefore could be responsible the relaxing effects of green tea and wild lettuce. It also prevents vitamin-A induced teratogenesis by blocking the conversion of retinol to its dangerous metabolite, all-trans-retinoic acid (Russo 2011, Taming THC: potential *cannabis* synergy and phytocannabinoid-terpenoid entourage effects, British Journal of Pharmacology, 163:1344-1364).

Cultivars of the Invention

*Cannabis* NWG331

*Cannabis* NWG331 is a hemp *Cannabis* cultivar with less than 0.2% of Δ9-Tetrahydrocannabinal (THC). The plants exhibit elevated levels of cannabidiol (CBD) and a ratio of CBD/THC of up to about 83:1. The cultivar produces plants with an average cannabidiol (CBD) content of more than 1.07% based upon total dry weight of the plant. It was generated from pedigree breeding with bulk and singleseed descent selections methods, and is genetically uniform and stable.

*Cannabis* NWG331 is a dioecious cultivar with male and female flowers that flowers at 58 days after planting. The plant height averages 170 cm to 190 cm and is medium height for a *Cannabis* cultivar. The plant has medium branching. The middle third of the plant is characterized by medium stem internode length, green stem color, green leaf color, medium leaf intensity, and medium leaf size. The cultivar has medium depth and width of stem grooves. Leaf anthocyanin coloration and male flower anthocyanin collation is absent. Hairs on the calyx are present but not in high density or length. Seed size is a thousand kernel weight of 13.5 grams and seed shape is spherical.

Table 1 below shows a typical profile of terpene content (ppm) for NWG331 as determined by head-space Gas Chromatography (Hs-GC) with flame ionization in female bud tissue.

TABLE 1

| | |
|---|---|
| a-pinene | 499.46 |
| camphene | 7.55 |
| sabinene | 6.87 |
| myrcene | 209.55 |
| b-pinene | 120.12 |
| a-phellandrene | 12.43 |
| 3-carene | 11.19 |
| a-terpenine | 11.74 |
| cineole | |
| ocimene-1 | 7.11 |
| limonene | 9.42 |
| p-cymene | |
| ocimene-2 | 446.16 |
| eucalyptol | 17.38 |
| g-terpenine | 10.00 |
| terpinolene | 99.04 |
| linalool | 19.01 |
| fenchone | 4.88 |
| isopulegol | 13.40 |
| borneol | 4.78 |
| terpineol | 18.83 |
| citronellol | 6.49 |
| geraniol | |
| citral-1 | |
| pulegone | |
| citral-2 | 8.20 |
| b-caryophyllene | 1163.76 |
| humulene | 309.15 |
| nerolidol-1 | 38.20 |
| nerolidol-2 | 29.75 |
| guaiol | 10.39 |
| caryophyllene oxide | 19.81 |
| a-bisabolol | 65.61 |

Table 2 shows a typical cannabinoid content estimate as determined by High-performance liquid chromatography (% dry wt) in female bud tissue harvested from NWG331.

TABLE 2

| THC % | THC-A % | THC-total | CBD % | CBD-A % | CBD-total | CBN % | CBG % | CBD:THC |
|---|---|---|---|---|---|---|---|---|
| 0.01 | 0.09 | 0.09 | 0.03 | 2.50 | 2.54 | 0.00 | 0.00 | 28.32 |

*Cannabis* NWG452

*Cannabis* NWG452 is a hemp *Cannabis* cultivar with less than 0.2% of Δ9-Tetrahydrocannabinal (THC). The plants exhibits elevated levels cannabidiol (CBD) and a ratio of CBD/THC of up to about 83:1. The cultivar produces plants with an average cannabidiol (CBD) content of more than 1.07% based upon total dry weight of the plant. It was generated from pedigree breeding with bulk and single-seed descent selections methods, and is genetically uniform and stable.

Table 3 below shows a typical profile of terpene content (ppm) for NWG452 as determined by head-space Gas Chromatography (Hs-GC) with flame ionization in female bud tissue.

TABLE 3

| | |
|---|---|
| a-pinene | 269.10 |
| camphene | 6.28 |

TABLE 3-continued

| | |
|---|---|
| sabinene | 3.83 |
| myrcene | 311.61 |
| b-pinene | 81.61 |
| a-phellandrene | 10.58 |
| 3-carene | 6.24 |
| a-terpenine | 7.84 |
| cineole | |
| ocimene-1 | 12.72 |
| limonene | 11.03 |
| p-cymene | |
| ocimene-2 | 281.22 |
| eucalyptol | 26.07 |
| g-terpenine | 5.86 |
| terpinolene | 48.13 |
| linalool | 12.63 |
| fenchone | 4.34 |
| isopulegol | |
| borneol | 10.72 |
| terpineol | 15.79 |
| citronellol | 5.91 |
| geraniol | |
| citral-1 | |
| pulegone | 2.04 |
| citral-2 | 8.67 |
| b-caryophyllene | 1079.27 |
| humulene | 300.55 |
| nerolidol-1 | 19.55 |
| nerolidol-2 | 62.85 |
| guaiol | 11.23 |
| caryophyllene oxide | 23.46 |
| a-bisabolol | 30.89 |

The terpene profile of NWG452, shows that its myrcene content is 50% higher relative to NWG331.

Table 4 shows a typical cannabinoid content estimate as determined by High-performance liquid chromatography (% dry wt) in female bud tissue harvested from NWG452

TABLE 4

| THC % | THC-A % | THC-total | CBD % | CBD-A % | CBD-total | CBN % | CBG % | CBD:THC |
|---|---|---|---|---|---|---|---|---|
| 0.00 | 0.10 | 0.10 | 0.01 | 2.82 | 2.83 | 0.00 | 0.00 | 28.0 |

Further Embodiments of the Invention

This invention is also directed to methods for producing a *Cannabis* plant by crossing a first parent *Cannabis* plant with a second parent *Cannabis* plant, wherein the first parent *Cannabis* plant or second parent *Cannabis* plant is the *Cannabis* plant from cultivar NWG331 or NWG452. Further, both the first parent *Cannabis* plant and second parent *Cannabis* plant may be from cultivar NWG331 or NWG452. Therefore, any methods using hemp *Cannabis* cultivars NWG331 or NWG452 are part of this invention, such as selfing, backcrosses, hybrid breeding, and crosses to populations. Plants produced using hemp *Cannabis* cultivars of the invention as at least one parent are within the scope of this invention.

In one aspect of the invention, methods for developing novel plant types are presented. In one embodiment the specific type of breeding method is pedigree selection, where both single plant selection and mass selection practices are employed. Pedigree selection, also known as the "Vilmorin system of selection," is described in Fehr, Walter; Principles of Cultivar Development, Volume I, Macmillan Publishing Co., which is hereby incorporated by reference.

In one embodiment, the pedigree method of breeding is practiced where selection is first practiced among $F_2$ plants. In the next season, the most desirable $F_3$ lines are first identified, and then desirable $F_3$ plants within each line are selected. The following season and in all subsequent generations of inbreeding, the most desirable families are identified first, then desirable lines within the selected families are chosen, and finally desirable plants within selected lines are harvested individually. A family refers to lines that were derived from plants selected from the same progeny row the preceding generation.

Using this pedigree method, two parents may be crossed using an emasculated female and a pollen donor (male) to produce $F_1$ offspring. The $F_1$ may be self-pollinated to produce a segregating $F_2$ generation. Individual plants may then be selected which represent the desired phenotype in each generation ($F_3$, $F_4$, $F_5$, etc.) until the traits are homozygous or fixed within a breeding population.

In addition to crossing, selection may be used to identify and isolate new *Cannabis* lines. In *Cannabis* selection, *Cannabis* seeds are planted, the plants are grown and single plant selections are made of plants with desired characteristics. Seed from the single plant selections may be harvested, separated from seeds of the other plants in the field and re-planted. The plants from the selected seed may be monitored to determine if they exhibit the desired characteristics of the originally selected line. Selection work is preferably continued over multiple generations to increase the uniformity of the new line.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding may be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program may include a periodic, objective evaluation of the efficiency of the breeding procedure. Evaluation criteria vary depending on the goal and objectives, but should include gain from selection per year based on comparisons to an appropriate standard, the overall value of the advanced breeding lines, and the number of successful cultivars produced per unit of input (e.g., per year, per dollar expended, etc.).

In one embodiment, promising advanced breeding lines are thoroughly tested and compared to appropriate standards in environments representative of the commercial target area(s). The best lines are candidates for new commercial cultivars; those still deficient in a few traits are used as parents to produce new populations for further selection.

These processes, which lead to the final step of marketing and distribution, usually take several years from the time the first cross or selection is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of *Cannabis* plant breeding is to develop new, unique and superior *Cannabis* cultivars. In one embodiment, the breeder initially selects and crosses two or more parental lines, followed by repeated selfing and selection, producing many new genetic combinations. The breeder can theoretically generate billions of different genetic combinations via crossing, selfing and mutations. Preferably, each year the plant breeder selects the germplasm to advance to the next generation. This germplasm may be grown under different geographical, climatic and soil conditions, and further selections are then made, during and at the end of the growing season.

In a preferred embodiment, the development of commercial *Cannabis* cultivars requires the development of *Cannabis* varieties, the crossing of these varieties, and the evaluation of the crosses. Pedigree breeding and recurrent selection breeding methods may be used to develop cultivars from breeding populations. Breeding programs may combine desirable traits from two or more varieties or various broad-based sources into breeding pools from which cultivars are developed by selfing and selection of desired phenotypes. The new cultivars may be crossed with other varieties and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population; then, beginning in the $F_3$, the best individuals in the best families are usually selected. Replicated testing of families, or hybrid combinations involving individuals of these families, often follows in the $F_4$ generation to improve the effectiveness of selection for traits with low heritability. At an advanced stage of inbreeding (e.g., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals may be identified or created by intercrossing several different parents. The best plants may be selected based on individual superiority, outstanding progeny, or excellent combining ability. Preferably, the selected plants are intercrossed to produce a new population in which further cycles of selection are continued.

Backcross breeding has been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent may be selected and repeatedly crossed (backcrossed) to the recurrent parent. The resulting plant is expected to have the attributes of the recurrent parent (e.g., cultivar) and the desirable trait transferred from the donor parent.

The single-seed descent procedure refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Isozyme Electrophoresis and RFLPs have been widely used to determine genetic composition. Shoemaker and Olsen, (Molecular Linkage Map of Soybean (*Glycine max*) p 6.131-6.138 in S. J. O'Brien (ed) Genetic Maps: Locus Maps of Complex Genomes, Cold Spring Harbor Laboratory Press, Cold Spring Harbor, N.Y., (1993)) developed a molecular genetic linkage map that consisted of 25 linkage groups with about 365 RFLP, 11 RAPD, three classical markers and four isozyme loci. See also, Shoemaker, R. C., RFLP Map of Soybean, p 299-309, in Phillips, R. L. and Vasil, I. K., eds. DNA-Based Markers in Plants, Kluwer Academic Press, Dordrecht, the Netherlands (1994).

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus in soybean with as many as 26 alleles. (Diwan, N. and Cregan, P. B., Theor. Appl. Genet. 95:22-225, 1997.) SNPs may also be used to identify the unique genetic composition of the invention and progeny varieties retaining that unique genetic composition. Various molecular marker techniques may be used in combination to enhance overall resolution.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the identification of markers which are closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding is another method of introducing new traits into *Cannabis* varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in Principles of Cultivar Development by Fehr, Macmillan Publishing Company, 1993.

The production of double haploids can also be used for the development of homozygous varieties in a breeding program. Double haploids are produced by the doubling of a set of chromosomes from a heterozygous plant to produce a completely homozygous individual. For example, see Wan et al., Theor. Appl. Genet., 77:889-892, 1989.

Descriptions of other breeding methods that are commonly used for different traits and crops can be found in one of several reference books (e.g., Principles of Plant Breeding John Wiley and Son, pp. 115-161, 1960; Allard, 1960; Simmonds, 1979; Sneep et al., 1979; Fehr, 1987; "Carrots and Related Vegetable Umbelliferae", Rubatzky, V. E., et al., 1999).

*Cannabis* is an important and valuable crop. Thus, a continuing goal of *Cannabis* plant breeders is to develop stable, high yielding *Cannabis* cultivars that are agronomically sound. To accomplish this goal, the *Cannabis* breeder preferably selects and develops *Cannabis* plants with traits that result in superior cultivars.

This invention also is directed to methods for producing a *Cannabis* cultivar plant by crossing a first parent *Cannabis* plant with a second parent *Cannabis* plant wherein either the first or second parent *Cannabis* plant is a *Cannabis* plant of the line NWG331 or NWG452. Further, both first and second parent *Cannabis* plants can come from the cultivar NWG331 or NWG452. Still further, this invention also is directed to methods for producing a cultivar NWG331 or NWG452-derived *Cannabis* plant by crossing cultivar NWG331 or NWG452 with a second *Cannabis* plant and growing the progeny seed, and repeating the crossing and growing steps with the cultivar NWG331 or NWG452-derived plant from 0 to 7 times. Thus, any such methods using the cultivar NWG331 or NWG452 are part of this invention: selfing, backcrosses, hybrid production, crosses to populations, and the like. All plants produced using cultivar NWG331 or NWG452 as a parent are within the scope of this invention, including plants derived from cultivar NWG331 or NWG452. Advantageously, the cultivar is used in crosses with other, different, cultivars to produce first generation ($F_1$) *Cannabis* seeds and plants with superior characteristics.

As used herein, the term plant includes plant cells, plant protoplasts, plant cell tissue cultures from which *Cannabis* plants can be regenerated, plant calli, plant clumps and plant cells that are intact in plants or parts of plants, such as embryos, pollen, ovules, flowers, seeds, roots, anthers, and the like.

As is well known in the art, tissue culture of *Cannabis* can be used for the in vitro regeneration of a *Cannabis* plant. Tissue culture of various tissues of *Cannabis* and regeneration of plants therefrom is well known and widely published. For example, reference may be had to Teng et al., HortScience. 1992, 27: 9, 1030-1032 Teng et al., HortScience. 1993, 28: 6, 669-1671, Zhang et al., Journal of Genetics and Breeding. 1992, 46: 3, 287-290, Webb et al., Plant Cell Tissue and Organ Culture. 1994, 38: 1, 77-79, Curtis et al., Journal of Experimental Botany. 1994, 45: 279, 1441-1449, Nagata et al., Journal for the American Society for Horticultural Science. 2000, 125: 6, 669-672. It is clear from the literature that the state of the art is such that these methods of obtaining plants are, and were, "conventional" in the sense that they are routinely used and have a very high rate of success. Thus, another aspect of this invention is to provide cells which upon growth and differentiation produce *Cannabis* plants having the physiological and morphological characteristics of variety NWG331 or NWG452.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as transgenes. Over the last fifteen to twenty years several methods for producing transgenic plants have been developed, and the present invention, in particular embodiments, also relates to transformed versions of the claimed line.

Plant transformation preferably involves the construction of an expression vector that will function in plant cells. Such a vector may comprise DNA comprising a gene under control of or operatively linked to a regulatory element (for example, a promoter).

The expression vector may contain one or more such operably linked gene/regulatory element combinations. The vector(s) may be in the form of a plasmid, and can be used alone or in combination with other plasmids, to provide transformed *Cannabis* plants, using transformation methods as described below to incorporate transgenes into the genetic material of the *Cannabis* plant(s).

Expression Vectors for *Cannabis* Transformation
Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley et al., Proc. Natl. Acad. Sci. U.S.A., 80:4803 (1983). Another commonly used selectable marker gene is the hygromycin phosphotransferase gene which confers resistance to the antibiotic hygromycin. Vanden Elzen et al., Plant Mol. Biol., 5:299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., Plant Physiol. 86:1216 (1988), Jones et al., Mol. Gen. Genet., 210:86 (1987), Svab et al., Plant Mol. Biol. 14:197 (1990<Hille et al., Plant Mol. Biol. 7:171 (1986). Other selectable marker genes confer resistance to herbicides such as glyphosate, glufosinate or broxynil. Comai et al., Nature 317:741-744 (1985), Gordon-Kamm et al., Plant Cell 2:603-618 (1990) and Stalker et al., Science 242:419-423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., Somatic Cell Mol. Genet. 13:67 (1987), Shah et al., Science 233:478 (1986), Charest et al., Plant Cell Rep. 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include beta.-glucuronidase (GUS), .beta.-galaetesidase, luciferase and chloramphenicol, acetyltransferase. Jefferson, R. A., Plant Mol. Biol. Rep. 5:387 (1987), Teen et al., EMBO J. 8:343 (1989), Koncz et al., Proc. Natl. Acad. Sci U.S.A. 84:131 (1987), DeBlock et al., EMBO J. 3:1681 (1984).

Recently, in vivo methods for visualizing GUS activity that do not require destruction of plant tissue have been made available. Molecular Probes publication 2908, Imagene Green™, p. 1-4 (1993) and Naleway et al., J. Cell Biol. 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., Science 263:802 (1994). GFP and mutants of GFP may be used as screenable markers.

Promoters

Genes included in expression vectors preferably are driven by nucleotide sequence comprising a regulatory element, for example, a promoter. Several types of promoters are now well known in the transformation arts, as are other regulatory elements that can be used alone or in combination with promoters.

As used herein, promoter includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive promoter" is a promoter which is active under most environmental conditions.

A. Inducible Promoters

An inducible promoter is operably linked to a gene for expression in *Cannabis*. Optionally, the inducible promoter is operably linked to a nucleotide sequence encoding a signal sequence which is operably linked to a gene for expression in *Cannabis*. With an inducible promoter the rate of transcription increases in response to an inducing agent. Any inducible promoter can be used in the instant invention. See Ward et al., Plant Mol. Biol. 22:361-366 (1993). Exemplary inducible promoters include, but are not limited to, that from the ACEI system which responds to copper (Meft et al., PNAS 90:4567-4571 (1993)); In2 gene from maize which responds to benzenesulfonamide herbicide safeners (Hershey et al., Mol. Gen Genetics 227:229-237 (1991) and Gatz et al., Mol. Gen. Genetics 243:32-38 (1994)) or Tet repressor from Tn10 (Gatz et al., Mol. Gen. Genetics 227:229-237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., Proc. Natl. Acad. Sci. U.S.A. 88:0421 (1991).

B. Constitutive Promoters

A constitutive promoter may be operably linked to a gene for expression in *Cannabis* or the constitutive promoter may operably linked to a nucleotide sequence encoding a signal sequence which is operably linked to a gene for expression in *Cannabis*.

Many different constitutive promoters can be utilized in the instant invention. Exemplary constitutive promoters include, but are not limited to, the promoters from plant viruses such as the 35S promoter from CaMV (Odell et al., Nature 313:810-812 (1985) and the promoters from such genes as rice actin (McElroy et al., Plant Cell 2:163-171 (1990)); ubiquitin (Christensen et al., Plant Mol. Biol. 12:619-632 (1989) and Christensen et al., Plant Mol. Biol. 18:675-689 (1992)); pEMU (Last et al., Theor. Appl. Genet. 81:581-588 (1991)); MAS (Velten et al., EMBO J. 3:2723-2730 (1984)) and maize H3 histone (Lepetit et al., Mol. Gen. Genetics 231:276-285 (1992) and Atanassova et al., Plant Journal 2 (3): 291-300 (1992)). The ALS promoter, Xba1/

NcoI fragment 5' to the *Brassica napus* ALS3 structural gene (or a nucleotide sequence similarity to said XbaI/NcoI fragment), represents a particularly useful constitutive promoter. See PCT application WO96/30530.

C. Tissue-specific or Tissue-preferred Promoters

A tissue-specific promoter may be operably linked to a gene for expression in *Cannabis*. Optionally, the tissue-specific promoter is operably linked to a nucleotide sequence encoding a signal sequence which is operably linked to a gene for expression in *Cannabis*. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., Science 23:476-482 (1983) and Sengupta-Gopalan et al., Proc. Natl. Acad. Sci. U.S.A. 82:3320-3324 (1985)); a leaf-specific and light-induced promoter such as that from cab or rubisco (Simpson et al., EMBO J. 4(11):2723-2729 (1985) and Timko et al., Nature 318:579-582 (1985)); an anther-specific promoter such as that from LAT52 (Twell et al., Mol. Gen. Genetics 217:240-245 (1989)); a pollen-specific promoter such as that from Zm13 (Guerrero et al., Mol. Gen. Genetics 244:161-168 (1993)) or a microspore-preferred promoter such as that from apg (Twell et al., Sex. Plant Reprod. 6:217-224 (1993).

Signal Sequences for Targeting Proteins to Subcellular Compartments

Transport of protein produced by transgenes to a subcellular compartment such as the chloroplast, vacuole, peroxisome, glyoxysome, cell wall or mitochondroin or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., Plant Mol. Biol. 20:49 (1992), Close, P. S., Master's Thesis, Iowa State University (1993), Knox, C., et al., Structure and Organization of Two Divergent Alpha-Amylase Genes from Barley, Plant Mol. Biol. 9:3-17 (1987), Lerner et al., Plant Physiol. 91:124-129 (1989), Fontes et al., Plant Cell 3:483-496 (1991), Matsuoka et al., Proc. Natl. Acad. Sci. 88:834 (1991), Gould et al., J. Cell. Biol. 108:1657 (1989), Creissen et al., Plant J. 2:129 (1991), Kalderon, et al., A short amino acid sequence able to specify nuclear location, Cell 39:499-509 (1984), Steifel, et al., Expression of a maize cell wall hydroxyproline-rich glycoprotein gene in early leaf and root vascular differentiation, Plant Cell 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants that are harvested in a conventional manner, and a foreign protein then can be extracted from a tissue of interest or from total biomass. Protein extraction from plant biomass can be accomplished by known methods which are discussed, for example, by Heney and Orr, Anal. Biochem. 114:92-6 (1981).

According to a preferred embodiment, the transgenic plant provided for commercial production of foreign protein is *Cannabis*. In another preferred embodiment, the biomass of interest is seed. For transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons may involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes That Confer Resistance to Pests or Disease and That Encode:

A. Plant disease resistance genes. Plant defenses are often activated by specific interaction between the product of a disease resistance gene (R) in the plant and the product of a corresponding avirulence (Avr) gene in the pathogen. A plant line can be transformed with cloned resistance gene to engineer plants that are resistant to specific pathogen strains. See, for example Jones et al., Science 266:789 (1994) (cloning of the tomato Cf-9 gene for resistance to *Cladosporium fulvum*); Martin et al., Science 262:1432 (1993) (tomato Pto gene for resistance to *Pseudomonas syringae* pv. Tomato encodes a protein kinase); Mindrinos et al., Cell 78:1089 (1994) (*Arabidopsis* RSP2 gene for resistance to *Pseudomonas syringae*).

B. A *Bacillus thuringiensis* protein, a derivative thereof or a synthetic polypeptide modeled thereon. See, for example, Geiser et al., Gene 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

C. A lectin. See, for example, the disclosure by Van Damme et al., Plant Molec. Biol. 24:25 (1994), who disclose the nucleotide sequences of several *Clivia miniata* mannose-binding lectin genes.

D. A vitamin-binding protein such as avidin. See PCT application US93/06487, the contents of which are hereby incorporated by reference. The application teaches the use of avidin and avidin homologues as larvicides against insect pests.

E. An enzyme inhibitor, for example, a protease or proteinase inhibitor or an amylase inhibitor. See, for example, Abe et al., J. Biol. Chem. 262:16793 (1987) (nucleotide sequence of rice cysteine proteinase inhibitor), Huub et al., Plant Molec. Biol. 21:985 (1993) (nucleotide sequence of cDNA encoding tobacco proteinase inhibitor I), Sumitani et al., Biosci. Biotoch. Biochem. 57:1243 (1993) (nucleotide sequence of *Streptomyces nitrosporeus* α-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., Nature 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, J. Biol. Chem. 269:9 (1994) (expression cloning yields DNA coding for insect diuretic hormone receptor), and Pratt et al., Biochem. Biophys. Res. Comm. 163:1243 (1989) (an allostatin is identified in *Diploptera puntata*). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., Gene 116:165 (1992), for disclosure of heterologous expression in plants of a gene coding for a scorpion insectotoxic peptide.

I. An enzyme responsible for a hyper accumulation of a monterpene, a sesquiterpene, a steroid, hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23:691 (1993), who teach the nucleotide sequence of a cDNA encoding tobacco hookworm chitinase, and Kawalleck et al., Plant Molec. Biol. 21:673 (1993), who provide the nucleotide sequence of the parsley ubi4-2 polyubiquitin gene.

K. A molecule that stimulates signal transduction. For example, see the disclosure by Botella et al., Plant Molec. Biol. 24:757 (1994), of nucleotide sequences for mung *Cannabis* calmodulin cDNA clones, and Griess et al., Plant Physiol. 104:1467 (1994), who provide the nucleotide sequence of a maize calmodulin cDNA clone.

L. A hydrophobic moment peptide. See PCT application WO95/16776 (disclosure of peptide derivatives of tachyolesin which inhibit fungal plant pathogens) and PCT application WO95/18855 (teaches synthetic antimicrobial peptides that confer disease resistance), the respective contents of which are hereby incorporated by reference.

M. A membrane permease, a channel former or a channel blocker. For example, see the disclosure of Jaynes et al., Plant Sci 89:43 (1993), of heterologous expression of a cecropin-β, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. rev. Phytopathol. 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect. Cf Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., Nature 366:469 (1993), who show that transgenic plants expressing recombinant antibody genes are protected from virus attack.

Q. A developmental-arrestive protein produced in nature by a pathogen or a parasite. Thus, fungal endo-α-1, 4-D-polygalacturonases facilitate fungal colonization and plant nutrient release by solubilizing plant cell wall homo-α-1, 4-D-galacturonase. See Lamb at al., Bio/Technology 10:1436 (1992). The cloning and characterization of a gene which encodes a *Cannabis* endopolygalacturonase-inhibiting protein is described by Toubart et al., Plant J. 2:367 (1992).

R. A development-arrestive protein produced in nature by a plant. For example, Logemann et al., Bioi/Technology 10:305 (1992), have shown that transgenic plants expressing the barley ribosome-inactivating gene have an increased resistance to fungal disease.

S. A *Cannabis* mosaic potyvirus (LMV) coat protein gene introduced into *Lactuca sativa* in order to increase its resistance to LMV infection. See Dinant et al., Molecular Breeding. 1997, 3: 1, 75-86.

2. Genes that Confer Resistance to an Herbicide, for Example:

A. A herbicide that inhibits the growing point or meristem, such as an imidazalinone or a sulfonylurea. Exemplary genes in this category code for mutant ALS and AHAS enzyme as described, for example, by Lee et al., EMBO J. 7:1241 (1988), and Miki et al., Theor. Appl. Genet. 80:449 (1990), respectively.

B. Glyphosate (resistance impaired by mutant 5-enolpyruvl-3-phosphikimate synthase (EPSP) and aroA genes, respectively) and other phosphono compounds such as glufosinate (phosphinothricin acetyl transferase, PAT and *Streptomyces hygroscopicus* phosphinothricin-acetyl transferase PAT bar genes), and pyridinoxy or phenoxy propionic acids and cycloshexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. See also Umaballava-Mobapathie in Transgenic Research. 1999, 8: 1, 33-44 that discloses *Lactuca sativa* resistant to glufosinate. European patent application No. 0 333 033 to Kumada at al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al., DeGreef et al., Bio/Technology 7:61 (1989), describe the production of transgenic plants that express chimeric bar genes coding for phosphinothricin acetyl transferase activity. Exemplary of genes conferring resistance to phenoxy propionic acids and cycloshexones, such as sethoxydim and haloxyfop are the Acc1-S1, Acc1-S2 and Acc1-S3 genes described by Marshall et al., Theor. Appl. Genet. 83:435 (1992).

C. A herbicide that inhibits photosynthesis, such as a triazine (psbA and gs+ genes) and a benzonitrile (nitrilase gene). Przibilla et al., Plant Cell 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., Biochem. J. 285:173 (1992).

D. Acetohydroxy acid synthase, which has been found to make plants that express this enzyme resistant to multiple types of herbicides, has been introduced into a variety of plants. See Hattori et al., Mol. Gen. Genet. 246:419, 1995. Other genes that confer tolerance to herbicides include a gene encoding a chimeric protein of rat cytochrome P4507A1 and yeast NADPH-cytochrome P450 oxidoreductase (Shiota et al., Plant Physiol., 106:17, 1994), genes for glutathione reductase and superoxide dismutase (Aono et al., Plant Cell Physiol. 36:1687, 1995), and genes for various phosphotransferases (Datta et al., Plant Mol. Biol. 20:619, 1992).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,837; 5,767,373; and international publication WO 01/12825.

3. Genes that Confer or Contribute to a Value-Added Trait, Such as:

A. Increased iron content of the *Cannabis*, for example by transforming a plant with a soybean ferritin gene as described in Goto et al., Acta Horticulturae. 2000, 521, 101-109. Parallel to the improved iron content enhanced growth of transgenic *Cannabis* s was also observed in early development stages.

B. Decreased nitrate content of leaves, for example by transforming a *Cannabis* with a gene coding for a nitrate reductase. See for example Curtis et al., Plant Cell Report. 1999, 18: 11, 889-896.

C. Increased sweetness of the *Cannabis* by transferring a gene coding for monellin that elicits a flavor sweeter than sugar on a molar basis. See Penarrubia et al., Biotechnology. 1992, 10: 5, 561-564.

D. Modified fatty acid metabolism, for example, by transforming a plant with an antisense gene of stearyl-ACP desaturase to increase stearic acid content of the plant. See Knultzon et al., Proc. Natl. Acad. Sci. USA 89:2625 (1992).

E. Modified carbohydrate composition effected, for example, by transforming plants with a gene coding for an enzyme that alters the branching pattern of starch. See Shiroza et al., J. Bacteriol. 170:810 (1988) (nucleotide sequence of *Streptococcus* mutants fructosyltransferase gene), Steinmetz et al., Mol. Gen. Genet. 20:220 (1985) (nucleotide sequence of *Bacillus subtilis* levansucrase gene), Pen et al., Bio/Technology 10:292 (1992) (production of transgenic plants that express *Bacillus licheniformis*.alpha.-amylase), Elliot et al., Plant Molec. Biol. 21:515 (1993) (nucleotide sequences of tomato invertase genes), Sogaard et al., J. Biol. Chem. 268:22480 (1993) (site-directed mutagenesis of barley .alpha.-amylase gene), and Fisher et al., Plant Physiol. 102:1045 (1993) (maize endosperm starch branching enzyme II).

4. Genes that Control Male-Sterility

A. Introduction of a deacetylase gene under the control of a tapetum-specific promoter and with the application of the chemical N—Ac-PPT. See international publication WO 01/29237.

B. Introduction of various stamen-specific promoters. See international publications WO 92/13956 and WO 92/13957.

C. Introduction of the barnase and the barstar genes. See Paul et al., Plant Mol. Biol. 19:611-622, 1992).

Methods for *Cannabis* Transformation

Numerous methods for plant transformation have been developed, including biological and physical, plant transformation protocols. See, for example, Miki et al., "Procedures for Introducing Foreign DNA into Plants" in Methods in Plant Molecular Biology and Biotechnology, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick B. R. and Thompson, J. E. Eds. (CRC Press, Inc., Boca Raton, 1993) pages 89-119.

A. *Agrobacterium*-mediated Transformation

One method for introducing an expression vector into plants is based on the natural transformation system of *Agrobacterium*. See, for example, Horsch et al., Science 227:1229 (1985). Curtis et al., Journal of Experimental Botany. 1994, 45: 279, 1441-1449, Torres et al., Plant cell Tissue and Organic Culture. 1993, 34: 3, 279-285, Dinant et al., Molecular Breeding. 1997, 3: 1, 75-86. *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., Crit. Rev. Plant Sci. 10:1 (1991). Descriptions of *Agrobacterium* vector systems and methods for *Agrobacterium*-mediated gene transfer are provided by Gruber et al., supra, Miki et al., supra, and Moloney et al., Plant Cell Reports 8:238 (1989). See also, U.S. Pat. No. 5,591,616 issued Jan. 7, 1997.

B. Direct Gene Transfer

Several methods of plant transformation collectively referred to as direct gene transfer have been developed as an alternative to *Agrobacterium*-mediated transformation. A generally applicable method of plant transformation is microprojectile-mediated transformation wherein DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Russell, D. R., et al. Pl. Cell. Rep. 12(3, January), 165-169 (1993), Aragao, F. J. L., et al. Plant Mol. Biol. 20(2, October), 357-359 (1992), Aragao, F. J. L., et al. Pl. Cell. Rep. 12(9, July), 483-490 (1993). Aragao, Theor. Appl. Genet. 93: 142-150 (1996), Kim, J.; Minamikawa, T. Plant Science 117: 131-138 (1996), Sanford et al., Part. Sci. Technol. 5:27 (1987), Sanford, J. C., Trends Biotech. 6:299 (1988), Klein et al., Bio/Technology 6:559-563 (1988), Sanford, J. C., Physiol Plant 7:206 (1990), Klein et al., Biotechnology 10:268 (1992).

Another method for physical delivery of DNA to plants is sonication of target cells. Zhang et al., Bio/Technology 9:996 (1991). Alternatively, liposome or spheroplast fusion has been used to introduce expression vectors into plants. Deshayes et al., EMBO J., 4:2731 (1985), Christou et al., Proc Natl. Acad. Sci. U.S.A. 84:3962 (1987). Direct uptake of DNA into protoplasts using $CaCl_2$ precipitation, polyvinyl alcohol or poly-L-ornithine has also been reported. Hain et al., Mol. Gen. Genet. 199:161 (1985) and Draper et al., Plant Cell Physiol. 23:451 (1982). Electroporation of protoplasts and whole cells and tissues have also been described. Saker, M.; Kuhne, T. Biologia *Plantarum* 40(4): 507-514 (1997/98), Donn et al., In Abstracts of VIIth International Congress on Plant Cell and Tissue Culture IAPTC, A2-38, p 53 (1990); D'Halluin et al., Plant Cell 4:1495-1505 (1992) and Spencer et al., Plant Mol. Biol. 24:51-61 (1994). See also Chupean et al., Biotechnology. 1989, 7: 5, 503-508.

Following transformation of *Cannabis* target tissues, expression of the above-described selectable marker genes allows for preferential selection of transformed cells, tissues and/or plants, using regeneration and selection methods now well known in the art.

The foregoing methods for transformation would typically be used for producing a transgenic line. The transgenic line could then be crossed, with another (non-transformed or transformed) line, in order to produce a new transgenic *Cannabis* line. Alternatively, a genetic trait that has been engineered into a particular *Cannabis* cultivar using the foregoing transformation techniques could be moved into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

Gene Conversions

When the term *Cannabis* plant, cultivar or *Cannabis* line is used in the context of the present invention, this also includes any gene conversions of that line. The term gene converted plant as used herein refers to those *Cannabis* plants which are developed by a plant breeding technique called backcrossing wherein essentially all of the desired morphological and physiological characteristics of a cultivar are recovered in addition to the gene transferred into the line via the backcrossing technique. Backcrossing methods can be used with the present invention to improve or introduce a characteristic into the line. The term backcrossing as used herein refers to the repeated crossing of a hybrid progeny back to one of the parental *Cannabis* plants for that line. The parental *Cannabis* plant that contributes the gene for the desired characteristic is termed the nonrecurrent or donor parent. This terminology refers to the fact that the nonrecurrent parent is used one time in the backcross protocol and therefore does not recur. The parental *Cannabis* plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original cultivar of interest (recurrent parent) is crossed to a second line (nonrecurrent parent) that carries the single gene of interest to be transferred. The resulting progeny from this cross are then crossed again to the recurrent parent and the process is repeated until a *Cannabis* plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute traits or characteristics in the original line. To accomplish this, a gene or genes of the recurrent cultivar are modified or substituted with the desired gene or genes from the nonrecurrent parent, while retaining essentially all of the rest of the desired genetic, and therefore the desired physiological and morphological, constitution of the original line. The choice of the particular nonrecurrent parent will depend on the purpose of the backcross. One of the major purposes is to add some commercially desirable, agronomically important trait or traits to the plant. The exact backcrossing protocol will depend on the characteristics or traits being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many gene traits have been identified that are not regularly selected for in the development of a new line but that can be improved by backcrossing techniques. Gene traits may or may not be transgenic, examples of these traits include but are not limited to, herbicide resistance, resistance for bacterial, fungal, or viral disease, insect resistance, enhanced nutritional quality, industrial usage, yield stability, yield enhancement, male sterility, modified fatty acid metabolism, and modified carbohydrate metabolism. These genes are generally inherited through the nucleus. Several of these gene traits are described in U.S. Pat. Nos. 5,777,196; 5,948,957 and 5,969,212, the disclosures of which are specifically hereby incorporated by reference.

Tissue Culture

Further reproduction of the variety can occur by tissue culture and regeneration. Tissue culture of various tissues of *Cannabis* and regeneration of plants therefrom is well known and widely published. For example, reference may be had to Teng et al., HortScience. 1992, 27: 9, 1030-1032 Teng et al., HortScience. 1993, 28: 6, 669-1671, Zhang et al., Journal of Genetics and Breeding. 1992, 46: 3, 287-290, Webb et al., Plant Cell Tissue and Organ Culture. 1994, 38: 1, 77-79, Curtis et al., Journal of Experimental Botany. 1994, 45: 279, 1441-1449, Nagata et al., Journal for the American Society for Horticultural Science. 2000, 125: 6, 669-672, and Ibrahim et al., Plant Cell, Tissue and Organ Culture. (1992), 28(2): 139-145. It is clear from the literature that the state of the art is such that these methods of obtaining plants are routinely used and have a very high rate of success. Thus, another aspect of this invention is to provide cells which upon growth and differentiation produce *Cannabis* plants having the physiological and morphological characteristics of cultivar NWG331 or NWG452.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

Additional Breeding Methods

This invention also is directed to methods for producing a *Cannabis* plant by crossing a first parent *Cannabis* plant with a second parent *Cannabis* plant wherein the first or second parent *Cannabis* plant is a *Cannabis* plant of cultivar NWG331 or NWG452. Further, both first and second parent *Cannabis* plants can come from hemp *Cannabis* cultivars of the invention. Thus, any such methods using hemp *Cannabis* cultivars of the invention are part of this invention: selfing, backcrosses, hybrid production, crosses to populations, and the like. All plants produced using hemp *Cannabis* cultivars of the invention as at least one parent are within the scope of this invention, including those developed from cultivars derived from hemp *Cannabis* cultivars of the invention. Advantageously, this *Cannabis* cultivar could be used in crosses with other, different, *Cannabis* plants to produce the first generation ($F_1$) *Cannabis* hybrid seeds and plants with superior characteristics. The cultivar of the invention can also be used for transformation where exogenous genes are introduced and expressed by the cultivar of the invention. Genetic variants created either through traditional breeding methods using hemp *Cannabis* cultivars of the invention or through transformation of cultivar NWG331 or NWG452 by any of a number of protocols known to those of skill in the art are intended to be within the scope of this invention.

The following describes breeding methods that may be used with hemp *Cannabis* cultivars of the invention in the development of further *Cannabis* plants. One such embodiment is a method for developing cultivar NWG331 or NWG452 progeny *Cannabis* plants in a *Cannabis* plant breeding program comprising: obtaining the *Cannabis* plant, or a part thereof, of cultivar NWG331 or NWG452, utilizing said plant or plant part as a source of breeding material, and selecting a hemp *Cannabis* cultivars of the invention progeny plant with molecular markers in common with cultivar NWG331 or NWG452 and/or with morphological and/or physiological characteristics selected from the characteristics listed in Table 1. Breeding steps that may be used in the *Cannabis* plant breeding program include pedigree breeding, backcrossing, mutation breeding, and recurrent selection. In conjunction with these steps, techniques such as RFLP-enhanced selection, genetic marker enhanced selection (for example SSR markers) and the making of double haploids may be utilized.

Another method which may be used involves producing a population of hemp *Cannabis* cultivars of the invention-progeny *Cannabis* plants, comprising crossing cultivar NWG331 or NWG452 with another *Cannabis* plant, thereby producing a population of *Cannabis* plants, which, on average, derive 50% of their alleles from hemp *Cannabis* cultivars of the invention. A plant of this population may be selected and repeatedly selfed or sibbed with a *Cannabis* cultivar resulting from these successive filial generations. One embodiment of this invention is the *Cannabis* cultivar produced by this method and that has obtained at least 50% of its alleles from hemp *Cannabis* cultivars of the invention.

One of ordinary skill in the art of plant breeding would know how to evaluate the traits of two plant varieties to determine if there is no significant difference between the two traits expressed by those varieties. For example, see Fehr and Walt, Principles of Cultivar Development, p 261-286 (1987). Thus the invention includes hemp *Cannabis* cultivars of the invention progeny *Cannabis* plants comprising a combination of at least two cultivar NWG331 or NWG452 traits selected from the group consisting of those listed in Table 1 or the cultivar NWG331 or NWG452 combination of traits listed above, so that said progeny *Cannabis* plant is not significantly different for said traits than hemp *Cannabis* cultivars of the invention as determined at the 5% significance level when grown in the same environmental conditions. Using techniques described herein, molecular markers may be used to identify said progeny plant as a hemp *Cannabis* cultivars of the invention progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of hemp *Cannabis* cultivars of the invention may also be characterized through their filial relationship with hemp *Cannabis* cultivars of the invention, as for example, being within a certain number of breeding crosses of hemp *Cannabis* cultivars of the invention. A breeding cross is a cross made to introduce new genetics into the progeny, and is distinguished from a cross, such as a self or a sib cross, made to select among existing genetic alleles. The lower the number of breeding crosses in the pedigree, the closer the relationship between hemp *Cannabis* cultivars of the invention and its progeny. For example, progeny produced by the methods described herein may be within 1, 2, 3, 4 or 5 breeding crosses of hemp *Cannabis* cultivars of the invention.

The foregoing invention has been described in detail by way of illustration and example for purposes of clarity and understanding. However, it will be obvious that certain changes and modifications such as single gene modifications and mutations, somoclonal variants, variant individuals selected from large populations of the plants of the instant variety and the like may be practiced within the scope of the invention, as limited only by the scope of the appended claims.

Deposits

Applicant(s) made a deposit of at least 2500 seeds of Hemp *Cannabis* cultivars NWG331 and NWG452 with an International Depositary Authority as established under the Budapest Treaty according to 37 CFR 1.803(a)(1), at the National Collections of Industrial, Food and Marine Bacteria Ltd. (NCIMB) in Aberdeen Scotland, Accession No. NCIMB 43290 and NCIMB 43280. The NWG331 and NWG452 seeds deposited therewith on Nov. 23, 2018 and Nov. 22, 2018, respectively, were taken from the deposit maintained by New West Genetics, PO Box 1662 Fort Collins, Colorado 80522 since prior to the filing date of this application. Access to this deposit will be available during the pendency of the application to the Commissioner of Patents and Trademarks and persons determined by the Commissioner to be entitled thereto upon request. Upon issue of claims, the Applicant(s) will make available to the public, pursuant to 37 CFR 1.808, a deposit of at least 2500 seeds of cultivar NWG331 and NWG452 with an International Depositary Authority as established under the Budapest Treaty according to 37 CFR 1.803(a)(1), at the National Collections of Industrial, Food and Marine Bacteria Ltd. (NCIMB) in Aberdeen Scotland.

This deposit will be maintained in the depository, which is a public depository, for a period of 30 years, or 5 years after the most recent request, or for the enforceable life of the patent, whichever is longer, and will be replaced if it becomes nonviable during that period. Additionally, Applicants have or will satisfy all the requirements of 37 C.F.R. §§ 1.801-1.809, including providing an indication of the viability of the sample. Applicants have no authority to waive any restrictions imposed by law on the transfer of biological material or its transportation in commerce. Applicants do not waive any infringement of their rights granted under this patent or under the Plant Variety Protection Act (7 USC 2321 et seq.).

What is claimed is:

1. A non-transgenic *Cannabis* cultivar designated NWG331 or NWG452 with a THC content of 0.2% or less, wherein a representative sample of seed of said cultivar was deposited under Accession No. NCIMB 43290 or NCIMB 43280.

2. Seed of *Cannabis* cultivar designated NWG331 or NWG452, wherein a representative sample of seed of said cultivar was deposited under Accession No. NCIMB 43290 or NCIMB 43280.

3. A *Cannabis* plant, or a part thereof, produced by growing the seed of claim 2.

4. A tissue culture of cells produced from the plant of claim 3, wherein said cells of the tissue culture are produced from a plant part selected from the group consisting of embryo, meristematic cell, leaf, cotyledon, hypocotyl, stem, root, root tip, pistil, anther, flower, seed and pollen.

5. A protoplast produced from the plant of claim 3.

6. A protoplast produced from the tissue culture of claim 4.

7. A *Cannabis* plant regenerated from the tissue culture of claim 4, wherein the plant has all of the morphological and physiological characteristics of cultivar NWG331 or NWG452, wherein a representative sample of seed was deposited under Accession No. NCIMB 43290 or NCIMB 43280.

8. A method for producing a hybrid *Cannabis* seed, wherein the method comprises crossing the plant of claim 3 with a different *Cannabis* plant and harvesting the resultant $F_1$ hybrid *Cannabis* seed.

9. A hybrid *Cannabis* seed produced by the method of claim 8.

10. A hybrid *Cannabis* plant, or a part thereof, produced by growing said hybrid seed of claim 9.

11. A method of producing a male sterile *Cannabis* plant wherein the method comprises transforming the *Cannabis* plant of claim 3 with a nucleic acid molecule that confers male sterility.

12. A male sterile *Cannabis* plant produced by the method of claim 11.

13. A method for producing an herbicide resistant *Cannabis* plant wherein the method comprises transforming the *Cannabis* plant of claim 3 with a transgene, wherein the transgene confers resistance to an herbicide selected from the group consisting of imidazolinone, sulfonylurea, glyphosate, glufosinate, L-phosphinothricin, triazine and benzonitrile.

14. An herbicide resistant *Cannabis* plant produced by the method of claim 13.

15. A method of producing an insect resistant *Cannabis* plant wherein the method comprises transforming the *Cannabis* plant of claim 3 with a transgene that confers insect resistance.

16. An insect resistant *Cannabis* plant produced by the method of claim 15.

17. The *Cannabis* plant of claim 16 wherein the transgene encodes a Bacillus thuringiensis endotoxin.

18. A method of producing a disease resistant *Cannabis* plant wherein the method comprises transforming the *Cannabis* plant of claim 3 with a transgene that confers disease resistance.

19. A disease resistant *Cannabis* plant produced by the method of claim 18.

20. A method of producing a *Cannabis* plant with a value-added trait, wherein the method comprises transforming the *Cannabis* plant of claim 3 with a heterologous nucleic acid sequence.

21. A *Cannabis* plant with a value-added trait produced by the method of claim 20.

22. A *Cannabis* plant, or a part thereof, having all of the physiological and morphological characteristics of hemp *Cannabis* cultivars NWG331 or NWG452, wherein a representative sample of seed of the cultivar was deposited under Accession No. NCIMB 43290 or NCIMB 43280.

23. A method of introducing a desired trait into hemp *Cannabis* cultivars NWG331 or NWG452 wherein the method comprises:
   a) crossing a NWG331 or NWG452 plant grown from NWG331 or NWG452 seed, wherein a representative sample of seed was deposited under Accession No. NCIMB 43290 or NCIMB 43280, with a plant of another *Cannabis* cultivar that comprises a desired trait to produce $F_1$ progeny plants, wherein the desired trait is selected from the group consisting of altered terpene or cannabinoid composition, male sterility, herbicide resistance, insect resistance, and resistance to bacterial disease, fungal disease, or viral disease;
   b) selecting one or more progeny plants that have the desired trait to produce selected progeny plants;
   c) crossing the selected progeny plants with the NWG331 or NWG452 plants to produce backcross progeny plants;
   d) selecting for backcross progeny plants that have the desired trait and all of the characteristics of hemp *Cannabis* cultivars NWG331 or NWG452 listed in Table 1 or Table 3 to produce selected backcross progeny plants; and
   e) repeating steps (c) and (d) three or more times in succession to produce selected fourth or higher backcross progeny plants that comprise the desired trait and all of the characteristics of hemp *Cannabis* cultivars NWG331 or NWG452 listed in Table 1 or Table 3.

24. A *Cannabis* plant produced by the method of claim 23, wherein the plant has the desired trait and all of the characteristics of NWG331 or NWG452 hemp *Cannabis* cultivars listed in Table 1 or Table 3.

25. The *Cannabis* plant of claim 24, wherein the desired trait is herbicide resistance and the resistance is conferred to an herbicide selected from the group consisting of imidazolinone, sulfonylurea, glyphosate, glufosinate, L-phosphinothricin, triazine and benzonitrile.

26. The *Cannabis* plant of claim 24, wherein the desired trait is insect resistance and the insect resistance is conferred by a transgene encoding a Bacillus thuringiensis endotoxin.

27. The *Cannabis* plant of claim 24, wherein the desired trait is male sterility and the trait is conferred by a nucleic acid molecule.

28. A method of conferring aroma, flavoring, or desired health benefits to a beverage comprising;
   preparing said beverage with the *Cannabis* plant of claim 3 or parts thereof or compositions purified therefrom.

29. The method of claim 28 wherein said beverage is beer, wine, cider, distilled spirit, hard soda, soft drink, juice, water, or flavored water.

30. A method of preparing cannabinoid isolates or isolate formulations, wherein the method comprises:
   harvesting flower tissue from the plant of claim 3; and
   extracting cannabinoids from the flower tissue.

31. A method of producing a *Cannabis* plant with a modified terpene or cannabinoid profile wherein the method comprises genetically modifying the *Cannabis* plant of claim 3 with a nucleic acid molecule that modifies the terpene or cannabinoid profile.

32. A method of producing a *Cannabis* plant with a THC content of 0.2% or less comprising the steps of:
(a) crossing the plant of claim 3 with a second *Cannabis* plant to produce a progeny plant;
(b) crossing the progeny plant of step (a) with itself or the second *Cannabis* plant in step (a) to produce a seed;
(c) growing a progeny plant of a subsequent generation from the seed produced in step (b);
(d) crossing the progeny plant of a subsequent generation of step (c) with itself or the second *Cannabis* plant in step (a) to produce a *Cannabis* plant derived from the *Cannabis* NWG331 or NWG452 with a THC content of 0.2% or less.

33. A method for developing a *Cannabis* plant in a *Cannabis* plant breeding program, comprising applying plant breeding techniques comprising recurrent selection, backcrossing, pedigree breeding, marker enhanced selection, mutation breeding, or genetic modification to the *Cannabis* plant of claim 3, or its parts, to develop of a *Cannabis* plant with a THC content of 0.2% or less.

\* \* \* \* \*